United States Patent [19]

Brown et al.

[11] Patent Number: 5,102,905

[45] Date of Patent: Apr. 7, 1992

[54] THIENYL BENZOTHIENYL AND DIBENZOTHIENYL COMPOUNDS AS INHIBITORS OF ALDOSE REDUCTASE

[75] Inventors: Steven P. Brown; Anthony L. Cooper, both of Bude; Jethro L. Longridge, MacClesfield; Jeffrey Morris, Sandbach; John Preston, Knutsford, all of Great Britain

[73] Assignee: Imperial Chemical Industries PLC, London, England

[21] Appl. No.: 344,804

[22] Filed: Apr. 28, 1989

[30] Foreign Application Priority Data

Apr. 29, 1988 [GB] United Kingdom ............... 8810203

[51] Int. Cl.$^5$ .................... A61K 31/38; C07D 333/52
[52] U.S. Cl. ..................... 514/443; 549/42; 549/45; 549/47; 549/50; 549/52; 549/54; 549/55; 549/61; 549/62; 549/63; 549/64; 549/65; 549/66; 549/433; 549/435; 549/436; 549/438; 549/439; 549/440; 549/460; 549/467; 549/474; 549/476; 548/421; 548/429; 548/443; 548/453; 548/473; 548/476; 548/477; 548/567; 514/411; 514/418; 514/424; 514/425; 514/445; 514/463; 514/464; 514/469; 514/471; 514/473
[58] Field of Search ............ 549/61, 62, 63, 42, 549/45, 47, 50, 54, 55, 52, 64, 65, 66; 514/445, 443

[56] References Cited

U.S. PATENT DOCUMENTS

| | | | |
|---|---|---|---|
| 4,053,633 | 10/1977 | Goralski et al. | 514/709 |
| 4,309,554 | 1/1982 | Goralski | 549/62 |
| 4,670,470 | 6/1987 | Firestone | 514/665 |
| 4,831,045 | 5/1989 | Tanouchi et al. | 514/369 |

FOREIGN PATENT DOCUMENTS

| | | |
|---|---|---|
| 252640 | 6/1987 | European Pat. Off. . |
| 304190 | 8/1988 | European Pat. Off. . |

OTHER PUBLICATIONS

Rescueil Des Travaux Chimiques Des Pays-Bas, vol. 93, No. 1, 1974, pp. 11-14; J. J. Zeilstra et al.; "Chemistry of alpha-nitrosulfones Part III, A new convenient synthesis of α-nitrosulfones" Chemical Abstracts, vol. 104, No. 3, Jan. 20, 1986, p. 475, Abstract No. 19503d.
J. Chem. Soc., Chemical Communications, 1984, 670.
J. Organic Chemistry, 1978, 43, 3101.
J. Chem. Soc., Chemical Communications, 1978, 362.
J. Organic Chemistry, 1986, 51, 1012-1015.
Chemical Abstracts, vol. 104, Abstract No. 168055.
J. Prakt, Chem., 1920, 101, 136-137, (Chemical Abstracts vol. 15, pp. 1013-1014).
Rec. Trav. Chim. Pays Bas, 1974, 93, 11-14.
Chemical Abstracts, vol. 59, Abstract No. 6341g.
J. Polymer Science, Polymer Chemistry Edition, 1985, 23, 1963-1972.
J. Heterocyclic Chemistry, 1977, 14, 1415-1416.

Primary Examiner—Mukund J. Shah
Assistant Examiner—Jyothsna Venkat
Attorney, Agent, or Firm—Cushman, Darby & Cushman

[57] ABSTRACT

The invention concerns heterocyclic nitromethane derivatives of the formula 1 as defined hereinafter (and their non-toxic salts) wherein the heterocyclic moiety Q is thienyl, benzothienyl or dibenzothienyl and may bear a wide variety of optional substituents, together with pharmaceutical compositions containing them. The nitromethane derivatives are inhibitors of the enzyme aldose reductase and are of value in the treatment of certain complications of diabetes and galactosemia.

10 Claims, No Drawings

THIENYL BENZOTHIENYL AND DIBENZOTHIENYL COMPOUNDS AS INHIBITORS OF ALDOSE REDUCTASE

This invention concerns novel heterocyclic nitromethane derivatives which are inhibitors of the enzyme aldose reductase and which are of value, for example, in the treatment of certain peripheral effects of diabetes or galactosemia. A method of treating one more of such peripheral effects using a heterocyclic nitromethane derivative and pharmaceutical compositions containing such a derivative are also provided. In addition, the invention concerns novel processes for the manufacture of the said novel derivatives and for the preparation of medicaments containing any of the nitromethane derivatives.

The enzyme aldose reductase is responsible for the catalytic conversion of aldoses, such as glucose and galactose, to the corresponding alditols, such as sorbitol and galactitol respectively, in warm blooded animals such as man. Alditols penetrate cell membranes poorly and, once formed, tend to be removed only by further metabolism. Consequently, alditols tend to accumulate within cells which may in turn be sufficient to destroy or impair the function of the cells themselves. In addition, raised alditol levels may result in abnormal levels of their metabolites which may themselves impair or damage cellular function. The enzyme aldose reductase has a relatively low substrate affinity and is generally only effective in the presence of relatively large concentrations of aldose. Such large concentrations are present in the clinical conditions of diabetes (excessive glucose) and galactosemia (excessive galactose). Consequently, aldose reductase inhibitors are useful in the reduction or prevention of the development of those peripheral effects of diabetes or galactosemia which may be due in part to the accumulation of sorbitol or galactitol, respectively, in tissues such as the eye, nerve and kidney. Such peripheral effects include, for example, macular oedema, cataract, retinopathy, neuropathy and impaired neutral conduction.

Although a number of aldose reductase inhibitors have been discovered and clinically evaluated, there is a continuing need for alternative inhibitors. The present invention is based in part on this need and on our discovery of the unexpected inhibition of the enzyme aldose reductase by certain heteroaromatic nitromethane derivatives.

According to the invention there is provided a novel nitromethane derivative of the formula $Q.SO_2.CH_2.NO_2$ (formula I set out hereinafter) wherein Q is a mono-, di- or tricyclic heteroaromatic moiety of 5, 9 or 13 ring atoms, one of which atoms is oxygen sulphur or a group of the formula —NR—, and the remaining atoms of which are carbon; R is hydrogen, (1–6C)alkyl, phenyl or phenyl(1–4C)alkyl, the latter two of which may optionally bear 1 or 2 substituents independently selected from halogeno, (1–4C)alkyl and (1–4C)alkoxy; and wherein said heteroaromatic moiety Q may optionally bear up to three substituents independently selected from: halogeno, cyano, carboxy, alkylamino or dialkylamino of up to 6 carbon atoms, (1–6C)alkanoylamino, (1–6C)alkanoyl, (1–6C)alkyl, (2–6C)alkenyl, (3–CC)alkenyloxy, (1–6C)alkoxy, fluoro((1–4C)alkoxy, hydroxy(1–6C)alkyl, (1–4C)alkoxy(1–4C)alkyl, carbamoyl, sulphamoyl, (1–6C)alkoxycarbonyl, (1–4C)alkylenedioxy, (1–6C)alkanesulphonamido, alkyl or dialkylcarbamoyl of up to 7 carbon atoms, alkyl or dialkylsulphamoyl of up to 6 carbon atoms, groups of the formula $—S(O)_n.R^1$ [in which n is zero or the integer 1 or 2 and $R^1$ is (1–4C)alkyl], phenyl, benzyl, phenoxy, benzyloxy, benzamido and benzenesulphonamido, the benzene ring of which last six substituents may itself optionally bear 1 or 2 substituents independently selected from halogeno, (1–4C)alkyl and (1–4C)alkoxy substituents; and when Q is a di- or tricyclic heteroaromatic moiety, the optional substituents on Q are also independently selected from hydroxy, amino, nitro and fluoro(1–4C)alkyl; or a non-toxic salt thereof.

In this specification the term "alkyl" includes both straight and branched alkyl groups but references to individual alkyl groups such as "propyl" are specific for the straight chain ("normal") version only, any branched chain isomer such as "isopropyl" being referred to specifically. An analogous convention applies to other generic terms.

It is to be understood that, insofar as certain of the compounds of formula I defined above may exist in optically active or racemic forms by virtue of one or more substituents containing an asymmetric carbon atom, the invention includes in its definition of active ingredient any such optically active or racemic form which possesses the property of inhibiting the enzyme aldose reductase. The synthesis of optically active forms may be carried out by standard techniques or organic chemistry well known in the art, for example by synthesis from optically active starting materials or by resolution of a racemic form. Similarly, inhibitory properties against aldose reductase may be evaluated using the standard laboratory tests referred to hereinafter.

Particular values for the heteroaromatic moiety Q include, for example, furyl, thienyl, benzothienyl, benzofuranyl, dibenzothienyl and dibenzofuranyl as well as pyrrolyl, indolyl and carbazolyl bearing the substituent R on the ring nitrogen atom.

It will be understood that when the divalent group alkylenedioxy is present then in general Q may only bear one additional optional substituent and is preferably a di- or tricyclic heteroaromatic moiety.

Specific values for optional substituents on the heteroaromatic moiety Q include the following, by way of examples:

for halogeno: fluoro, chloro, bromo and iodo;

for alkylamino or dialkylamino of up to 6 carbon atoms: methylamino, ethylamino, propylamino, butylamino, dimethylamino, diethylamino and (methyl)(propyl)amino;

for (1–6C)alkanoylamino: (1–4C)alkanoylamino, such as formamido, acetamido and propionamido;

for (1–6C)alkanoyl: formyl, (1–4C)alkanoyl, (such as acetyl, propionyl, butyryl and 2,2-dimethylpropionyl);

for (1–6C)alkyl: (1–4C)alkyl, such as methyl, ethyl, propyl, isopropyl, butyl, sec-butyl and t-butyl;

for (2–6C)alkenyl: (1–4C)alkenyl, such as vinyl, allyl, 1-propenyl and 2-methyl-2-propenyl;

for (3–6C)alkenyloxy: allyloxy, 2-methyl-2-propenyloxy and 3-methyl-3-butenyloxy;

for fluoro(1–4C)alkyl: trifluoromethyl, pentafluoroethyl, 2,2,2-trifluoroethyl and 3,3,3-trifluoropropyl;

for fluoro(1–4C)alkoxy: trifluoromethoxy and pentafluoroethoxy;

for (1–6C)alkoxy: (1–4C)alkoxy, such as methoxy, ethoxy, propoxy, isopropoxy, butoxy and t-butoxy;

for hydroxy(1–6C)alkyl: hydroxy(1–4C)alkyl, such as hydroxymethyl, 1-hydroxyethyl, 2-hydroxyethyl and 3-hydroxypropyl;

for (1–4C)alkoxy((1–4C)alkyl: methoxymethyl, ethoxymethyl, 1-methoxyethyl, 2-methoxyethyl and 3-methoxypropyl;

for (1–6C)alkoxycarbonyl: (1–4C)alkoxycarbonyl, such as methoxycarbonyl, ethoxycarbonyl, isopropoxycarbonyl and t-butoxycarbonyl;

for (1–4C)alkylenedioxy: methylenedioxy, ethylenedioxy and isopropylidenedioxy, attached to adjacent carbon atoms on the aromatic moiety Q;

for (1–6C)alkanesulphonamido: (1–4C)alkanesulphonamido, such as methanesulphonamido, ethanesulphonamido and butanesulphonamido;

for alkyl or dialkylcarbamoyl of up to 7 carbon atoms: N-methylcarbamoyl, N,N-dimethylcarbamoyl, N-ethylcarbamoyl, N,N-diethylcarbamoyl and N,N-dipropylcarbamoyl;

for alkyl or dialkylsulphamoyl of up to 6 carbon atoms: N-methylsulphamoyl, N,N-dimethylsulphamoyl, N-ethylsulphamoyl, N-propylsulphamoyl and N-butylsulphamoyl;

for a group of the formula $-S(O)_n.R^1$ as defined above: methylthio, ethylthio, propylthio, butylthio, methylsulphinyl, ethylsulphinyl, methylsulphonyl and ethylsulphonyl; and for phenyl, benzyl, phenoxy, benzyloxy, benzamido or benzenesulphonamido optionally bearing halogeno, (1–4C)alkyl or (1–4C)alkoxy substituents: phenyl, phenoxy, benzyloxy, benzamido or benzenesulphonamido optionally bearing 1 or 2 substituents independently selected from fluoro, chloro, bromo, methyl, ethyl, methoxy and ethoxy.

A particular value for R when it is (1–6C)alkyl is, for example, (1–4C)alkyl such as methyl, ethyl, propyl or butyl; and when it is phenyl(1–4C)alkyl is, for example, benzyl, 1-phenylethyl or 2-phenylethyl.

A particular value for an optional substituent when R is phenyl or phenyl(1–4C)alkyl is, for example, fluoro, chloro, bromo, iodo, methyl, ethyl, methoxy or ethoxy.

Values for optional substituents on Q which are of particular interest are, for example, halogeno (especially bromo, chloro and iodo), (1–6C)alkanoyl (and especially 2,2-dimethylpropionyl, (1–6C)alkyl (and especially methyl), (1–6C)alkoxy (and especially methoxy and t-butoxy) and benzyl, the benzene ring of which may itself optionally bear 1 or 2 substituents independently selected from halogeno, (1–4C)alkyl and (1–4C)alkoxy.

A preferred value for Q is, for example, thienyl or benzothienyl.

One particular group of novel compounds of the invention of particular interest comprises thiophenes or furans of the formula II or III (set out hereinafter) wherein X is selected from hydrogen, halogeno, cyano, (1–6C)alkyl, (1–6C)alkanoyl, (1–6C)alkoxy and benzyl, the latter itself optionally bearing 1 or 2 substituents independently selected from halogeno, (1–4C)alkyl and (1–4C)alkoxy; and $X^1$ is hydrogen, halogeno, or (1–6C)alkyl; together with the non-toxic salts thereof.

Still further groups of novel compounds of the invention comprises those compounds of the formula I wherein Q is:

a) benzo[b]furan or benzo[b]thiophene; and
b) indolyl or N-[(1–6C)alkyl]indolyl;

and in each group, Q bears 1 or 2 optional substituents independently selected from any of the values defined hereinabove for X; together with the non-toxic salts thereof.

A preferred value for X is, for example, hydrogen, chloro, bromo, iodo, methyl, methoxy, t-butoxy or 2,2-dimethylpropionyl.

It will be understood that when Q is a bicyclic or tricyclic heteroaromatic moiety, the $-SO_2.CH_2.NO_2$ group may be located in either the heterocylic or benzene rings.

Novel compounds of particular interest include those described in the accompanying Examples hereafter, of which those described in Examples 1, 2, 9, 11, 13, 19, 25, 28 and 32 are of special interest and are provided, together with their non-toxic salts, as a further feature of the invention.

The invention further includes pharmaceutical compositions comprising a compound of the formula I or a non-toxic salt thereof, defined above, together with a pharmaceutically acceptable diluent or carrier. The compositions of the invention may be in various conventional forms. Thus, they may be in a form suitable for oral use (for example as tablets, lozenges, hard or soft capsules, aqueous or oily suspensions, emulsions, dispersible powders or granules, syrups or elixirs), for topical use (for example as creams, ointments, gels or aqueous or oily solutions or suspensions) or for parenteral administration (for example as a sterile aqueous or oily solution for intravenous, subcutaneous, intramuscular or intravascular dosing) or as a suppository for rectal dosing.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a table formulation include, for example, inert diluents such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as arachis oil, liquid paraffin or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharin or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, or esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art. Topical formulations for administration to the eye will generally be in the form of an ointment, gel or sterile solution buffered at an opthalmically acceptable pH, for example in the range pH 7.0–7.6.

The amount of active ingredient that is combined with one or more excipients to produce a single dosage form will necessarily vary depending upon the host treated and the particular route of administration. For example, a formulation intended for oral administration to humans will generally contain for example from 0.5 mg to 1 g of active agent compounded with an appropriate and convenient amount of excipients which may vary from about 5 to about 98 percent by weight of the total composition. Dosage unit forms will generally contain about 1 mg to about 500 mg of an active ingredient.

Suitable non-toxic salts include, for example, pharmaceutically acceptable salts such as alkali metal (such as potassium or sodium), alkaline earth metal (such as calcium or magnesium), ammonium and aluminum salts, and salts with organic bases affording physiologically acceptable cations, such as salts with methylamine, dimethylamine, trimethylamine, piperidine and morpholine. In addition, for those active ingredients which are sufficiently basic (for example those which contain an alkylamino or dialkylamino group), suitable non-toxic salts include, for example, pharmaceutically and physiologically acceptable acid-addition salts such as salts with hydrogen halides, sulphuric acid, phosphoric acid, citric acid and maleic acid.

The novel compounds of the invention may be obtained by standard procedures of organic chemistry already known for the production of structurally analogous compounds, for example by one or more of the procedures reviewed in the paper by Zeilstra et alia in *Rec. Trav. Chim. Pays Bas* 1974, 93, 11–14. Such procedures are provided as a further feature of the invention and are illustrated by the following procedure in which Q has any of the meanings defined hereinbefore.

(a) Reacting an alkali metal sulphinate of the formula $Q.SO_2^- M^+$ (formula IV) wherein $M^+$ is an alkali metal cation and especially sodium or potassium, with nitromethane and iodine in the presence of an alkali metal (1-6C)alkoxide such as potassium t-butoxide or sodium methoxide. The reaction is preferably carried out in the presence of a suitable polar solvent, for example, dimethylformamide (DMF) or 1,3-dimethyl-3,4,5,6-tetrahydro-2(1H)-pyrimidinone (DMPU) (which are preferred) or N-methyl-2-pyrrolidone, and at a temperature in the range, for example, $-30°$ to $20°$ C. and, conveniently, at about $0°$ C. The nitromethane is generally present in an excess.

The alkali metal sulphinates may be obtained, for example, from the corresponding sulphinic acids of the formula $Q.SO_2H$ by reaction with the appropriate alkali metal hydroxide or (1-6C)alkoxide such as sodium or potassium methoxide or ethoxide. The sulphinic acids may themselves be obtained from the corresponding sulphonyl chlorides of the formula $Q.SO_2Cl$ by a conventional reduction using aqueous sodium sulphite or zinc dust and water. The sulphonyl chlorides may often be obtained by direct chlorosulphonation of the appropriate compound of the formula Q.H using an excess of chlorosulphonic acid, or by sulphonation of the appropriate compound of the formula Q.H to give the sulphonic acid of the formula $Q.SO_3H$ which is then converted to the sulphonyl chloride, for example, by reaction with phosphorus pentachloride. Alternatively, the sulphinates of formula IV may frequently be obtained, for example, by lithiation of the appropriate heterocyclic compound of the formula Q.H followed by reaction with sulphur dioxide and conversion to the required alkali metal salt as necessary, for example the sodium salt as illustrated in Example 3 hereinafter.

(b) Reacting a sulphone of the formula $Q.SO_2.CH_3$ (formula V) with a (1-5C)alkyl nitrate, such as ethyl, propyl, isopropyl or amyl nitrate, in the presence of a strong base.

A particularly suitable strong base is, for example, an alkali metal (1-6C)alkane such as butyllithium.

The reaction is preferably carried out int he presence of a suitable solvent or diluent, for example an ether such as tetrahydrofuran or t-butyl methyl ether, and at a temperature in the range, for example, $-80°$ to $10°$ C. The necessary sulphones of the formula V may be made by standard procedures well known in the art, for example by oxidation of the corresponding methylthio compound of the formula $Q.S.CH_3$ (formula VI) using analogous conditions to those described for process (c) below.

(c) Oxidizing a thioether of the formula $Q.S.CH_2NO_2$ (formula VII).

Suitable oxidizing agents include those which are well known in the art for the conversion of thio to sulphonyl groups and which are compatible with the presence of other sensitive functional groups which may be present as substituents on Q. Thus, for example, hydrogen peroxide, an organic peracid (such as a perbenzoic or peracetic acid) or lead tetraacetate may be used. Alternatively an alkali metal periodate (such as sodium metaperiodate), persulphate (such as potassium monopersulphate) or permanganate (such as potassium permanganate), or gaseous oxygen in the presence of a suitable catalyst such as platinum, may be employed. The oxidation is preferably carried out in a suitable conventional solvent or diluent for such oxidations, for example in acetic or propionic acid, and at a temperature in the general range, for example $0°$ to $80°$ C.

In certain cases, the corresponding sulphoxide derivative of the thioester of formula VII may be formed as an isolable intermediate. The process of the invention also includes the oxidation of such a sulphoxide intermediate to a sulphone of formula I, for example, by reaction with an alkali metal permanganate (such as potassium permanganate) in a suitable solvent such as aqueous acetic acid and at a temperature in the range, for example, $20°$ to $80°$ C.

The starting thioethers of formula VII may be obtained by conventional procedures of organic chemistry, for example, from a potassium or sodium salt of the corresponding thiols of the formula Q.SH (formula VIII) by conversion to the corresponding thioacetic acids of the formula $Q.S.CH_2.CO_2H$ (formula IX) or a (1-4C)alkyl ester thereof, such as methyl or ethyl ester) by reaction with chloro- or bromo-acetic acid (or a (1-4C)alkyl ester thereof) in the presence of a suitable base. The acid IX (or a (1-4C)alkyl ester thereof) is then reacted with a (1-5C)alkyl nitrate and an alkali metal (1-6C)alkane, for example isopropyl nitrate and butyllithium, under similar conditions to those used for process (b) above, to give the alkali metal salt of the corresponding 2-nitroacetic acid of the formula $Q.S.CH(NO_2).CO_2H$ (formula XI) (or of the (1-4C)alkyl ester thereof). The acids of the formula XI are unstable and readily decarboxylate. Acidification of the alkali metal salt of an acid of formula XI allows the isolation of a thioether of formula VII. An ester of an acid of formula XI may be hydrolysed, for example, using aqueous base, to the acid of formula XI and then acidified to produce a thioether of formula VII. The esters of the acids of formula XI may also conveniently be obtained by reacting the appropriate (1-4C)alkyl nitroacetate with the required sulphenyl chloride of the formula Q.SCl (formula XII) in the presence of a base such as potassium fluoride. The thiols of formula VIII may be obtained by conventional procedures of heterocyclic chemistry, for example as illustrated in the accompanying Examples.

The thioethers of the formula VII may also conveniently be obtained by reacting the appropriate compound of the formula Q.SH (formula VIII) with nitromethane in the presence of a suitable oxidizing agent (such as sodium or potassium ferricyanide), generally in an aqueous or partially aqueous medium, under basic conditions, in the presence of an organic solvent (such as dietyl ether), and at a temperature in the general range, for example, $0°$ to $25°$ C.

Alternatively, the thioethers of the formula VII may be obtained by reacting the appropriate compound of the formula $Q.S.CH_3$ (formula VI) with a halogenonitromethane (such as bromonitromethane) at a temperature in the general range of $90°$ to $180°$ C. and in the absence of any solvent or diluent (or in the presence of a high boiling diluent such as diphenyl ether).

(d) Reacting an alkali metal sulphinate of the formula $Q.SO_2^-M^+$ (formula IV) wherein $M^+$ is an alkali metal cation (and especially sodium or potassium), with a halogenonitromethane (such as bromonitromethane).

The reaction mixture is preferably with irradiated with light and the process is generally performed in the presence of a suitable polar solvent (such as DMF or DMPU), and at a temperature in the general range, for example, $-30°$ C. to $40°$ C.

(e) When a compound in which Q is an indolyl or carbazolyl group bearing up to 3 optional substituents and bearing the substituent R on the ring nitrogen as defined hereinbefore is required, reacting a compound of the formula I, in which Q is the correspondingly substituted indolinyl or 1,2,3,4-tetrahydrocarbazolyl group, with a dehydrogenating agent (such as 2,3-dichloro-5,6-dicyano-1,4-benzoquinone), preferably in the presence of a high-boiling insert organic solvent (such as xylene) and at a temperature in the general range of $90°$-$180°$ C.

It will be appreciated that in the formula I compounds of the invention Q may bear a wide variety of reactive substituents. Accordingly, it may be necessary to protect one or more such reactive substituents in a conventional manner at some stage prior to carrying out one of the above procedures (a)-(e) and then to remove to protecting group as a final step. Thus, for example, a hydroxy substituent may be protected using, for example, an acyl (such as acetyl, benzoyl or methylsulphonyl), t-butyl, alkyl, benzyl or trialkylsilyl (such as t-butyldimethylsilyl) protecting group; an amino substituent may be protected using, for example, an acyl (such as acetyl or benzoyl) or (1-4C)alkoxy.carbonyl (such as methoxycarbonyl, ethoxycarbonyl or t-butoxycarbonyl); a ketone group may be protected as its ketal (for example its ketal with 2,2-dimethylpropane-1,3-diol); and a carboxy substituent may be protected, for example, in the form of its (1-4C)alkyl (especially methyl, ethyl or t-butyl) or benzyl ester. The appropriate protecting groups and the procedures necessary for the protection and deprotection of reactive substituents are well described in standard text-books of organic chemistry. Accordingly, the invention also includes a development of one of the processes (a) to (e) for the production of a compound of formula I, as defined hereinbefore, which is characterised by using a starting material of the formula IV, V or VII, respectively, in which one or more reactive substituents present as substituents on Q (such as hydroxy, amino or carboxy) have been protected with appropriate protecting groups, and carrying out the appropriate removal of the protecting group as a final step.

Whereafter, when a compound of formula I in which R is (1-6C)alkyl or optionally substituted phenyl(1-4-C)alkyl is required, the corresponding compound of formula I wherein R is hydrogen is alkylated, for example by reaction with a (1-6C)alkyl or optionally substituted phenyl(1-4C)alkyl halide (such as an alkyl iodide or bromide or a phenylalkyl chloride or bromide). The reaction is generally performed in the presence of a strong base, for example an alkali metal hydride (such as sodium hydride) or using the preformed alkali metal salt (such as the lithium, sodium or potassium salt) of the compound of formula I in which R is hydrogen and in a suitable solvent or diluent such as N,N-dimethylformamide, tetrahydrofuran or t-butyl methyl ether and at a temperature in the general range, for example, 0°-60° C.

Whereafter, when a compound in which Q bears a halogeno or nitro substituent is required, it may be obtained, for example, by using a direct halogenation or nitration procedure well known in the art, for example bromination in acetic acid at a temperature in the general range 0°-40° C. as illustrated in Example 10 hereinafter.

Whereafter, when a non-toxic salt is required, a compound of formula I may be reacted with an appropriate base having a non-toxic cation, or, when Q bears a basic substituent (such as amino, alkylamino or dialkylamino) a non-toxic, acid-addition salt may be prepared by reaction with an appropriate acid having a non-toxic anion.

Many of the starting materials referred to herein are novel, for example the thioethers of the formula $Q.S.CH_2.NO_2$ (formula VII), and the sulphinic acids of the formula $Q.SO_2H$ together with their alkali metal salts of the formula $Q.SO_2^-M^+$ (formula IV) wherein M is an alkali metal cation, and are provided as a further feature of the invention.

As stated previously, the compounds of formula I inhibit the enzyme aldose reductase. The compounds are thus of value, for example, in treating those diseases or conditions which are caused by excessive quantities of the products such as sorbitol formed in the body by processes catalysed by the enzyme aldose reductase.

The property of inhibiting the enzyme aldose reductase in vivo may be demonstrated in the following standard laboratory test:

Rats are made diabetic (as evidenced by severe glucosuria being present) by dosing with streptozotocin. The animals are then dosed daily with the test compound for one, two or five days. The animals are then sacrificed 2-6 hours after the final dose and the eye lenses and/or sciatic nerves are removed. After a standard work-up procedure the residual sorbitol levels in each tissue are determined by gas liquid chromatography after conversion to the polytrimethylsilyl derivatives. Inhibition of aldose reductase in vivo can then be assessed by comparing the residual sorbitol levels in tissues from the dosed diabetic group of rats with those of an undosed group of diabetic rats and an undosed, normal group of rats.

The property of inhibiting the enzyme aldose reductase may also be demonstrated in vitro. Thus, in a standard procedure partially purified aldose reductase is isolated in known manner from bovine lenses. The percentage inhibition of this enzyme's ability in vitro to catalyse the reduction of aldoses to polyhydric alcohols, and particularly to reduce glucose or sorbitol, caused by a test compound can then be determined using standard spectrophotometric methods.

By way of illustration of the aldose reductase inhibitory properties of compounds of formula I, the compound of Example 1 had an $IC_{50}$ of $5.4 \times 10^{-8}$ M in the above in vitro test and an $ED_{50}$ of 2.1 mg/kg in the above in vivo test.

In general, compounds of the formula I show significant inhibition in one or both of the above mentioned tests, for example, significant inhibition in the in vivo test at a dose (generally p.o.) of 100 mg/kg or much less with no evidence of overt toxicity, and with an $IC_{50}$ in the above mentioned in vitro test of about $10^{-6}$ M or much less.

The compounds of formula I will primarily be administered systemically (generally by mouth) to a warm-blooded animal to produce a therapeutic or prophylactic effect mediated by inhibition of the enzyme aldose reductase, for example, at a daily dose in the range of 1 to 40 mg/kg. In man it is envisaged that a total daily dose in the range 15 to 800 mg. per man will be administered, given if necessary, in divided doses. However, the precise amount of compound administered will naturally vary somewhat, for example, with the age and sex of the patient and the severity and extent of the condition being treated.

The compounds of formula I may also be administered topically, for example by topical administration direct to the tissue or organ in which inhibition of the enzyme is required, for example by topical administration to the eye. The precise amount of compound administered will necessarily depend on the formulation used. Thus, for example, when a solution is administered a concentration of the compound containing up to 0.01% by weight will generally be used. Similarly, when an ointment is administered a concentration of the compound of up to 2% by weight will generally be used. Topical formulations of compounds of formula I may be administered to the eye of an animal, for example, man or dog, requiring treatment and/or prevention of diabetic cataracts or retinopathy, in a conventional manner, for example, using a drop or eyewash topical formulation.

The compositions may also contain one or more other agents which are known to have a useful effect in the treatment of diabetes or galactosemia, for example a hypoglycemia agent such as tolbutamide, chlorpropamide or glybenclamide.

The invention will now be illustrated by the following non-limiting Examples in which, unless otherwise stated:

(i) all evaporations were carried out by rotary evaporation in vacuo.

(ii) all operations were carried out at room temperature, that is in the range 18°-26° C.;

(iii) column and flash chromatography was carried out on silica (Merck Art. 7734) and medium pressure liquid chromatography (MPLC) on silica (Merck Art. 9385), both materials available from E Merck and Co., Darmstadt, West Germany; and preparative layer chromatography (PLC) was carried out on silica coated plates (Schleicher & Schull Art. G1505/LS254), available from Schleicher & Schull, Dassel, West Germany;

(iv) the purity of chemical products was assessed by nuclear magnetic resonance (NMR) spectroscopy, thin layer chromatographic analysis, mass spectroscopy and/or microanalysis;

(v) NMR spectra were determined in deuterochloroform ($CDCl_3$) at 200 MHz and are given in delta values (parts per million) relative to tetramethylsilane as standard; conventional abbreviations for signal types are used, such as s, singlet; d, doublet; dd, doublet of doublets; br, broad; et cetera;

(vi) petroleum ether (b.p. 60°-80° C.) is referred to as "petrol 60°-80°";

(vii) yields are for illustration only and are not necessarily the maximum attainable by diligent process development; and (viii) all end-products had microanalyses and NMR spectra consistent with the indicated structures.

EXAMPLE 1

A solution of nitromethane (5.92 g) in dry dimethylformamide (DMF) (20 ml) was added dropwise with ice-cooling to a solution of potassium t-butoxide (4.93 g) in dry DMF (100 ml). The mixture was stirred for 15 minutes and then treated with a solution of sodium thiophene-2-sulphinate [prepared from the corresponding sulphinic acid (6.5 g) as described below] also in dry DMF (80 ml) followed by iodine (11.18 g). The mixture was stirred in an ice-bath for 1.5 hours and then treated with 20% w/v sodium metabisulphite solution (50 ml) to discharge the dark colour. The mixture was then diluted with water (1 liter), acidified with concentrated hydrochloric acid and then extracted with ether (3×100 ml). The combined ether extracts were washed with water, dried over magnesium sulphate and evaporated to leave the crude product as a yellow oil (4.6 g).

This was purified by flash chromatography on a column (50×70 mm diameter) of silica using methylene chloride as eluant. The material (1.17 g) thus obtained was further purified by column chromatography on silica, eluting with 50-75% methylene chloride in hexane, followed by crystallisation from hexane to give 2-(nitromethylsulphonyl)thiophene as a white crystalline solid (350 mg), m.p. 32°-34° C.; NMR: 5.66 (s, 2H), 7.2-7.3 (t,1H), 7.85-7.95 (quartet of doublets, 8 lines, 2H); mass spectrum m/e (chemical ionisation): 225 $(M+NH_4)^+$, (electron impact): 207 ($M^+$); microanalysis, found: C,29.0; H,2.6; N,6.4%; $C_5H_{NO4}S_2$ requires: C,29.0; H,2.4; N,6.8%.

The sulphinate salt was obtained as follows:

Thiophene-2-sulphonyl chloride (10 g) was added in one portion to a stirred solution of sodium sulphite heptahydrate (32.8 g) and sodium bicarbonate (10.92 g) in water (100 ml) at 70° C. The solution was stirred at this temperature for 1.5 hours. It was then cooled rapidly, taken to pH 1 by addition of cold 60% sulphuric acid and the mixture extracted with ether (3×100 ml). The combined either extracts were dried over magnesium sulphate and evaporated to leave thiophene-2-sulphinic acid as an oil (6.5 g). This was dissolved in methanol (70 ml) containing sodium methoxide derived from the addition of sodium metal (1.21 g). After 10 minutes the methanol was removed in vacuo to leave a solid residue of sodium thiophene-2-sulphinate, which was dried by azeotropic distillation with toluene in vacuo and used directly in the above reaction.

EXAMPLE 2

Using a similar procedure to that described in Example 1, but starting from 2-chlorothiophene-5-sulphonyl chloride (10 g) and with intermediate formation of 2-chlorothiophene-5-sulphinic acid, there was obtained with flash chromatography, recrystallisation from 5% ethyl acetate/hexane followed by column chromatography and further recrystallisation from ethyl acetate/hexane, 2-chloro-5-(nitromethylsulphonyl)thiophene as a white crystalline solid (136 mg), m.p. 75°-77° C.; NMR: 5.66 (s,2H), 7.1 (d,1H), 7.67 (d,1H); m/e (electron impact): 241 ($M^+$); microanalysis, found: C,25.0; H,1,8; N,5.5%; $C_5H_4ClNO_4S_2$ requires: C,24.9; H,1.7; N,5.8%.

EXAMPLE 3

Using a similar procedure to that described in Example 1 but starting from sodium benzofuran-2-sulphinate (7.0 g) and performing the reaction at −20° C. over 1 hour, there was obtained after chromatography and recrystallisation from ethyl acetate/hexane using activated charcoal, 2-(nitromethylsulphonyl)benzofuran as a white solid (0.4 g), m.p. 70°-72° C.; NMR: 5.8 (s,2H), 7.3-7.85 (m, 5H); m/e (electron impact) 241 ($M^+$); microanalysis, found: C,45.1, H,3.0; N,5.8%; $C_9H_7NO_5S$ requires: H,2.9; N,5.8%.

The sulphinate salt used in the above example was prepared as follows:

A solution of butyllithium in hexane (1.5 M) (46.7 ml) was added to a stirred solution of benzofuran (10 g) in sodium-dried ether (200 ml) at room temperature. A slight exotherm caused the solution to reflux for about 5 minutes. The solution was stirred for 20 minutes at room temperature, cooled to −20° C. to −30° C. and then treated with gaseous sulphur dioxide (ca. 12 g) whereupon the lithium sulphinate salt started to precipitate out immediately. The suspension was stirred rapidly for one hour and then allowed to warm up to room temperature. The solid lithium benzofuran-2-sulphinate was filtered off and washed with dry acetone and sodium-dried ether. After drying in vacuo at 30° C. for 24 hours over phosphorous pentoxide, this crude product weighed 11 g. The mass spectrum (electon impact) showed m/e 181 for the sulphinate ion and m/e (181-$SO_2$).

The above lithium salt was dissolved in water and the solution acidified to PH1 and extracted with ether. The combined extracts were dried and evaporated. The resultant benzofuran-2-sulphinic acid obtained was then converted to the corresponding sodium salt using an analogous procedure to that described in Example 1. Sodium benzofuran-2-sulphinate was thus obtained as a solid (11.15 g) which was used without purification in the above reaction.

EXAMPLE 4

A solution of potassium peroxymonosulphate ('Oxone' trade mark, 600 mg, 0.98 mmol) in water (1.5 ml) was added in one portion to a vigorously stirred solution of 5-(nitromethylthio)benzo[b]thiophene, (150 mg, 0.67 mmol) in 1,2-dimethoxyethane (3 ml). The mixture was stirred for 20 hours and then diluted with water (10 ml). The aqueous mixture was extracted with dichloromethane (2×10 ml). The combined extracts were washed with brine (2×10 ml) and dried (Na$_2$SO$_4$) and the solvent evaporated. The brown residue (100 mg) was purified by flash chromatography, using dichloromethane as eluant to give 5-(nitromethyhlsulphonyl)-benzo [b]thiophene as a white crystalline solid (50 mg, after recrystallisation from toluene), m.p. 105°–106° C.; NMR: 5.62 (s,2H), 7.52 (d,1H), 7.70 (d,1H), 7.84–7.88 (dd,1H), 8.10–8.15 (d,1H), 8.45 (d,1H); m/e (electron impact): 257 (M+); (chemical ionisation) 275 (M+NH$_4$)+; microanalysis, found: C,41.7; H,2.7; N,5.0%; C$_9$H$_7$NO$_4$S$_2$ requires: C,42.0; H,2.7; N,5.4%.

The starting material was obtained as follows:

(i) 5-aminobenzo[b]thiophene (6.3 g, 42 mmol) was added in portions to a stirred solution of 98% w/v sulphuric acid (23 ml) and water (120 ml) maintained at 0°–5° C. A solution of sodium nitrite (3.5 g, 50 mmol) and water (15 ml) was then added dropwise and the mixture was stirred for 30 minutes at 0° C. The excess nitrous acid was destroyed by addition of an excess of sulphamic acid. The reaction mixture (containing the 5-diazonium sulphate derivative) was added to a stirred mixture of 2-mercaptoacetic acid (3.8 ml, 55 mmol), basic copper carbonate (2.8 g) and acetone (40 ml) at 0° C. After 1 hour the mixture was warmed to ambient temperature. Ethyl acetate (50 ml) was added and the insoluble material was removed by filtration through diatomaceous earth. The filtrate was extracted with ethyl acetate. The combined ethyl acetate extract was then extracted with a saturated solution of sodium hydrogen carbonate. The combined aqueous extracts were acidified to pH 4 with 2 M hydrochloric acid and again extracted with ethyl acetate. The combined extracts were washed with brine, dried (Na$_2$SO$_4$) and the solvent removed by evaporation. The residue was purified by flash chromatography using 80:20 v/v toluene/ethyl acetate as eluant. There was thus obtained 2-(benzo[b]-thien-5-ylthio)acetic acid (A) as a white, crystalline solid (1.6 g, after recrystallisation from toluene/hexane), m.p. 94°–95° C.; NMR (90 MHz): 3.7 (s,2H), 7.3–8.0 (m,5H), 8.4–9.2 (br, 1H): m/e (chemical ionisation): 242 (M+NH$_4$)+; microanalysis, found: C,53.8; H,3.6%, C$_{10}$H$_8$O$_2$S$_2$ requires: C,53.6; H,3.6%.

(ii) A 1.55 M solution of butyllithium in hexane (6.2 ml, 10 mmol) was added to a stirred solution of A (1.1 g, 5 mmol) in anhydrous tetrahydrofuran (30 ml) maintained at −40° C. under an atmosphere of argon. When the addition was complete, the mixture was stirred for 1 hour at −5° C. Isoamyl nitrate (2 ml, 15 mmol) was then added dropwise to the stirred mixture at −5° C. The reaction mixture was then stirred for a further 2 hours at −5° to 0° C. The mixture (containing lithium 2-(benzo[b]thien-5-ylthio)-2-nitroacetate) was acidified to pH 2 by addition of 2 M hydrochloric acid and was then left for 30 minutes at ambient temperature, after which time evolution of carbon dioxide (produced by decarboxylation of 2-(benzo[b]thien-5-ylthio)-2-nitroacetic acid) had ceased. Water (50 ml) was then added and the mixture was extracted with ethyl acetate. The combined extracts were washed successively with a saturated solution of sodium hydrogen carbonate, then with brine, dried (Na$_2$SO$_4$), and the solvent removed by evaporation. The residual oil was purified by flash chromatography using 75:25 v/v hexane/toluene as eluant to give 5-(nitromethylthio)benzo[b]thiophene as a yellow oil; NMR (90 MHz): 5.5 (s,2H), 7.2–8.0 (m,5H); m/e (electron impact); 225 (M+).

EXAMPLE 5

A 3% aqueous solution of potassium permanganate (83 ml, 16.2 mmol) was added to a stirred solution of 4-(nitromethylsulphinyl)dibenzofuran (3.72 g, 13.5 mmol) at 50° C. in acetic acid (100 ml). The reaction mixture was stirred for 1 hour at ambient temperature and then treated with a saturated aqueous solution of sodium metabisulphite until colourless. The reaction mixture was then diluted with water (200 ml). The solid material was removed by filtration, air dried and recrystallised from toluene/cyclohexane to give 4-(nitromethylsulphonyl)dibenzofuran as a white crystalline solid (2.95 g), m.p. 162°–165° C.; NMR (DMSOd$_6$): 6.80 (s,2H) 7.48–8.79 (m,7H); m/e (electron impact): 291 (M+); microanalysis, found: C,53.6; H,3.0; N,4.7%; C$_{13}$H$_9$NO$_5$S requires: C,53.6; H,3.1; N,4.8%.

The starting material was obtained as follows:

(i) Dibenzofuran (25 g, 148 mmol) was stirred in dry tetrahydrofuran (THF) at 2° C. under an argon atmosphere and a 1.55 M solution of butyllithium in hexane (96 ml, 144 mmol) was added at such a rate that the temperature did not exceed 5° C. The reaction mixture was stirred at ambient temperature for 4.5 hours, cooled to −66° C. and powdered sulphur (4.8 g, 150 mmol) was slowly added, causing an exotherm to −62° C. The reaction was stirred and allowed to warm up to ambient temperature during 1 hour. The dark brown solution was added to water (500 ml). The organic layer was separated and washed with water (100 ml and 50 ml). The combined aqueous layers were washed with ether (100 ml). The aqueous layer (containing the lithium salt of dibenzofuran-4-thiol) was treated with a solution of potassium carbonate (10.3 g, 75 mmol) and chloroacetic acid (14.1 g, 149 mmol) in water (50 ml). The residual solvent was removed by evaporation. The resultant aqueous solution was treated with 2 M hydrochloric acid (150 ml). The solid precipitate was collected by filtration, air dried and recrystallised from toluene/cyclohexane to give 2-(dibenzofuran-4-ylthio)acetic acid (B) as an off-white solid (28.2 g); microanalysis, found: C,65.0; H,3.8%; C$_{14}$H$_{10}$O$_3$S requires: C,65.1; H,3.9%.

(ii) A 1.55 M solution of butyllithium in hexane (50 ml, 78 mmol) was added to dry THF (200 ml) at −60° C. under an atmosphere of argon. A solution of the thioacetic acid (B) (10.0 g, 39 mmol) in dry THF (60 ml) was added to this stirred solution during 20 minutes at such a rate that the temperature did not exceed −50° C. The yellow solution was stirred at −40° C. for 1 hour and then isoamyl nitrate (15.6 ml, 117 mmol) was added during 7 minutes. The reaction mixture was stirred and allowed to attain ambient temperature during 2 hours. It was then acidified with 2 M hydrochloric acid (100 ml) in order to decarboxylate the intermediate 2-nitroacetic acid derivative. When gas evolution had ceased, water (500 ml) and ethyl acetate (200 ml) were added and organic layer separated. This aqueous layer was extracted with ethyl acetate (50 ml). The combined ethyl acetate layers were washed with saturated sodium hydrogen carbonate solution (5×50 ml) and then the solvent was removed by evaporation. The residue was purified by flash chromatography using 5:95 v/v ethyl acetate/hexane as eluants, to give 4-(nitromethylthio)-dibenzofuran (C) as a white solid (3.87 g, after recrystallisation from cyclohexane), m.p. 78°–79° C.; microanalysis, found: C,60.2; H,3.5; N,5.3%; C$_{13}$H$_9$NO$_3$S requires: C,60.2; H,3.5; N,5.4%.

(iii) A solution of potassium peroxymonosulphate ('Oxone', trade mark; 12.8 g, 20.8 mmol) in water (52 ml) was added in one portion to a stirred solution of the nitromethylthio derivative (C) (3.64 g, 14.1 mmol) in 1.2-dimethoxyethane (75 ml). The mixture was stirred vigorously for 18 hours. The reaction mixture was diluted with water (300 ml). The solid obtained was collected by filtration, air dried and recrystallised from toluene to give 4-(nitromethylsulphinyl)dibenzofuran as a white solid (3.82 g), m.p. 174°–176° C.; microanalysis found: C,56.8; H,3.2; N,5.0%; $C_{13}H_9NO_4S$ requires: C,56.7; H,3.3 N,5.1%.

EXAMPLE 6

Using a similar procedure to that described in Example 5 but starting from 2-methoxy-3-(nitromethylsulphinyl)dibenzofuran (0.97 g, 3.2 mmol), there was obtained 2-methoxy-3-(nitromethylsulphonyl)dibenzofuran as a white solid (787 mg, after recrystallisation from toluene), m.p. 172°–714° C.; NMR (DMSO-$d_6$): 4.1 (s,3H) 6.6 (s,2H) 7.45–8.15 (m,6H); m/e (electron impact): 321 (M+); microanalysis, found: C,52.7; H,3.5; N, 4.3%; $C_{14}H_{11}NO_6S$ requires: C,52.3; H,3.5; N,4.4%.

The starting material was obtained as follows:

(i) 3-Amino-2-methoxydibenzofuran (10 g, 46.9 mmol) was stirred in a mixture of acetic acid (100 ml), water (120 ml) and concentrated sulphuric acid (23.5 ml) at 80° C. for 15 minutes. The mixture was cooled to 0° C. and a solution of sodium nitrite (3.9 g, 57 mmol) in water (15 ml) was added at such a rate that the temperature did not exceed 4° C. The mixture was cooled −5° C. After 15 minutes, the excess sodium nitrite was decomposed by addition of an excess of sulphamic acid (0.9 g). The solution of the diazonium salt was added in a steady stream to a stirred mixture of basic copper carbonate (2.9 g) in water (50 ml) at 0° C. to which had been added thioglycolic acid (4.1 ml, 59 mmol). The mixture was allowed to attain ambient temperature during 30 minutes and then stirred thus for 4.5 hours until gas evolution (nitrogen) had ceased. Ethyl acetate (100 ml) was then added and solid material removed by filtration through diatomaceous earth, washing the filter pad with ethyl acetate. The organic layer was separated from the filtrate and washings extracted with 2 M aqueous sodium hydroxide solution (7×100 ml). Those extracts containing product [as indicated by thin layer chromatography (tlc) of a neutralised aliquot on silica, using ethyl acetate as eluant] were combined, washed with ether (100 ml), then neutralised with 2 M hydrochloric acid in the presence of ether (100 ml). This ether layer was separated, washed with brine and the solvent evaporated. Toluene was added to the residue and then removed by evaporation to remove remaining acetic acid. The residual yellow-brown solid was recrystallised from toluene to give 2-(2-methoxydibenzofuran-3-yl-thio)acetic acid (D) as a tan solid (2.60 g), m.p. 180°–182° C., which was used without further purification.

(ii) Using a similar procedure to that described in part (ii) of Example 5 for the preparation of the starting material C in Example 5, the thioacetic acid D (3.4 g, 11.8 mmol) was converted to 2-methoxy3-(nitromethylthio)dibenzofuran (E) which was obtained as a pale yellow solid (1.20 g), m.p. 115°–117° C. (after flash chromatography using 1:9 v/v ethyl acetate/hexane as eluant and crystallisation from cyclohexane); microanalysis, found: C,57.9; H,3.8; N,4.7%; $C_{14}H_{11}NO_4S$ requires: C,58.1; H,3.8; N,4.8%.

(iii) Using a similar procedure to that described in part (iii) of Example 5, the nitromethylthio derivative E (1.11 g, 3.8 mmol) was converted to 2-methoxy-3-(nitomethylsulphinyl)dibenzofuran, which was obtained as an off-white solid (1.01 g), m.p. 172°–174° C. after crystallisation from toluene; microanalysis, found: C,55.1; H,3.5; N,4.5%; $C_{14}H_{11}NO_5S$ requires: C,55.1; H,3.6; N,4.6%.

EXAMPLE 7

Using a similar procedure to that described in Example 5 but starting from 4-(nitromethylsulphinyl)dibenzothiophene (211 mg, 0.73 mmol), there was obtained 4-(nitromethylsulphonyl)dibenzothiophene as a white solid (51 mg), m.p. 145°–146° C., after flash chromatography using 1:4 v/v ethyl acetate/hexane as eluant and crystallisation of the initial product from toluene/cyclohexane; the material had NMR (DMSO$d_6$): 6.7 (s,2H), 7.6–8.9 (m,7H); m/e (electron impact): 307 (M+); and microanalysis, found: C,51.0; H,2.9; N,4.4%; $C_{13}H_9NO_4S_2$ requires: C,50.8; H,3.0; N,4.6%.

The 4-(nitrometyylsulphinyl)dibenzothiophene was obtained as follows:

(i) Using a similar procedure to that described in part (i) of Example 5 for the preparation of the thioacetic acid B, 4-aminodibenzothiophene (13.7 g, 68.8 mmol) was converted to 2-(dibenzothien-4-ylthio)acetic acid (F), which was obtained as a yellow solid (3.96 g, after crystallisation from toluene) and which was used without further purification.

(ii) Using a similar procedure to that described in part (ii) of Example 5 for the preparation of the nitromethylthio derivative C, the thioacetic acid F (3.8 g, 13.9 mmol) was converted to 4-(nitromethylthio)dibenzothiophene (G) (0.81 g), m.p. 85°–86° C. (after flash chromatography using 5:95 v/v ethyl acetate/hexane as eluant and crystallisation from toluene/cyclohexane); microanalysis, found: C,56.9; H,3.3; N,4.8%, $C_{13}H_9NO_2S_2$ requires: C,56.7; H,3.3; N,5.1%.

(iii) Using a similar procedure to that described in part (iii) of Example 5, nitromethylthio derivative G (780 mg, 2.8 mmol) was converted to 4-(nitromethylsulphinyl)dibenzothiophene, which was obtained as a white solid (243 mg), m.p. 151°–152° C. (after flash chromatography and crystallisation from toluene); microanalysis, found: C,53.2; H,3.0; N,4.6%; $C_{13}H_9NO_3S_2$ requires: C,53.6; H,3.1; N,4.8%.

EXAMPLE 8

A solution of potassium peroxymonosulphate ('Oxone' trade mark; 22.2 g, 36.1 mmol) in water (50 ml) was added in one portion to a vigorously stirred solution of 3-(nitromethylthio)indole (2.5 g, 12 mmol) in methanol (50 ml). The mixture was stirred for 16 hours, then diluted with water (100 ml) and extracted with ethyl acetate. The combined extracts were dried (MgSO$_4$) and the solvent removed by evaporation. The residual oil was purified by MPLC, eluting with ethyl acetate/hexane (3:7 v/v, gradually increasing the polarity to 2:3 v/v) to give 3-(nitromethylsulphonyl)indole (0.35 g), m.p. 181°–182° C. (after trituration with hexane/ether); microanalysis, found: C,45.5; H,3.4; N,11.2%; $C_9H_8N_2O_4S$ requires: C,45.0; H,3.3; N,11.7%.

The starting material was obtained as follows:

(i) A 1 M solution of potassium hydroxide (32 ml, 32 mmol) was added to a stirred suspension of S-(3-indolyl)isothiouronium iodide (3.2 g, 10 mmol) in ethanol (7.5 ml) under an atmosphere of argon, followed by chloroacetic acid (1.05 g, 11 mmol). The mixture was heated at 80° C. for 4 hours, allowed to cool and volatile material evaporated. The residue was treated with water (100 ml). The mixture was separated by filtration. The ice-cooled filtrate was acidified to pH 2 with 2 M hydrochloric acid.

The mixture was extracted with ethyl acetate (2×75 ml). The combined extracts were washed with water, brine, then dried (MgSO$_4$) and evaporated. The residue was triturated with ether/hexane to give (3-indolythio)acetic acid (H) as a solid (1.6 g).

(ii) A 1.1 M solution of butyllithium in hexane (258 ml: 284 mmol) was added dropwise to a stirred solution of the thioacetic acid H (19.1 g; 92.3 mmol) in anhydrous THF (500 ml) maintained at −40° C. under an atmosphere of argon. When the addition was complete, the temperature of the mixture was allowed to rise to −5° C. Propyl nitrate (37 ml; 371 mmoL) was added dropwise to the stirred mixture at −5° C., which was then stirred for 2 hours at 0° C. The mixture was acidified to pH 2 with 2 M hydrochloric acid, diluted with water, and extracted with ethyl acetate. The combined extracts were dried (MgSO$_4$) and evaporated. The residual liquid was purified by MPLC, eluting with ethyl acetate/hexane (1:9 v/v, gradually increasing the polarity to 1:4 v/v) to give 3-(nitromethylthio)indole as a red oil (2.5 g), MMR: 5.28 (s,2H), 7.2–7.8 (m,5H), 8.3–8.75 (br,1H), which was used without further purification.

EXAMPLE 9 m-Chloroperbenzoic acid (80% strength, 4.9 g) was added in portions to a stirred solution of 2-methoxy-5-nitromethylthio)thiophene (2.33 g) in chloroform (150 ml). The solution was stirred for 16 hours. The precipitate of m-chlorobenzoic acid was removed by filtration. The filtrate was washed with 20% w/v sodium metabisulphite solution, separated by filtration and the filtrate evaporated. The residue was purified by column chromatography using methylene chloride as eluant followed by recrystallisation from ethanol to give 2-methoxy-5-(nitromethylsulphonyl)thiophene as a solid (1.4 g), m.p. 70°–71° C.; NMR (90 MHz): 4.0 (s,3H), 5.57 (s,2H), 6.35 (d,1H), 7.55 (d,1H); m/e (electron impact): 237 (M$^+$); microanalysis, found: C,30.0; H,2.9; N,5.5%; C$_6$H$_7$NO$_5$S$_2$ requires: C,30.4; H,2.98; N,5.9%.

The starting material was prepared as follows:

A hexane/THF solution of lithium diisopropylamide was obtained by adding butyllithium (1.55 M hexane solution, 86.45 ml) to a stirred solution of diisopropylamine (10.1 g) in THF (100 ml) at −70° C. under an argon atmosphere. After 1 hour at −70° C., a solution of 2-(2-methoxythien-5-ylthio)acetic acid (obtained as described in West German OLS no. 1512272; 10.91 g) was added to the diisopropylamide solution during 20 minutes at −70° C. After 2 hours at this temperature, it was allowed to warm up to −40° C. Isoamyl nitrate (21.2 ml) was then added. The mixture was stirred at −40° C. for 2 hours and then at ambient temperature for 16 hours. The mixture was acidified to pH 2 with 2 M hydrochloric acid and stirred for 1 hour, during which time the intermediate 2-nitro-2-(2-methoxythien-5-ylthio)acetic acid underwent decarboxylation. The mixture was added to water (100 ml) and extracted with ethyl acetate. The combined organic layers were washed first with saturated sodium bicarbonate solution (200 ml) (to remove unreacted acidic starting material) and then with 2 M sodium hydroxide (2×200 ml). The latter washings were acidified to pH 2 with 2 M hydrochloric acid and extracted with ether (2×300 ml). The combined extracts were dried (MgSO$_4$) in the presence of activated charcoal and evaporated. The residual oil was purified by column chromatography on silica (300 g) using 15% v/v ethyl acetate/hexane as eluant to give 2-methoxy-5-(nitromethylthio)thiophene (2.9 g) as an oil; NMR (90 MHz): 3.9 (s,3H), 5.25 (s,2H), 6.1 (d,1H), 7.0 (d,1H).

EXAMPLE 10

A solution of bromine (0.254 g) in acetic acid (2 ml) was added to a stirred solution of 2-methoxy-5-(nitromethylsulphonyl)thiophene (0.39 g) in acetic acid (8 ml). After 1 hour the mixture was quenched with water (10 ml). The yellow precipitate was collected by filtration and recrystallised from ethanol to give 3-bromo-2-methoxy-5-(nitromethylsulphonyl)thiophene as a white solid (0.12 g) m.p. 120°–121° C.; m/e (electron impact): 315, 317 [mean M$^+$ for Br=80 is 316]; NMR (90 MHz): 4.1 (s,3H), 5.60 (s,2H), 7.22 (s,1H); microanalysis, found: C,23.1; H,1.8; N,4.1%; C$_6$H$_6$BrNO$_5$S$_2$ requires C,22.8; H,1.9; N,4.4%.

EXAMPLE 11

Using an analogous procedure to that described in Example 9, 2-methyl-5-(nitromethylthio)thiophene (0.51 g) was oxidized to give 2-methyl-5-(nitromethylsulphonyl)thiophene following chromatography as in Example 9 and recrystallisation from ethyl acetate/hexane. The compound was obtained in 66% yield as a white solid, m.p. 73°–74° C.; NMR: 2.62 (s,3H), 5.61 (s,2H), 6.92 (dd,1H), 7.66 (d,1H); m/e (electron impact) 221 (M$^+$); microanalysis, found C,32.3, H,3.2, N,6.0%; C$_6$H$_7$NO$_4$S$_2$ requires: C,32.6; H,3.2; N,6.3%.

The starting material was obtained using a similar procedure to that described for that in Example 9, but starting with 2-(2-methylthien-5-ylthio)acetic acid (described in Zh. Obsch. Khim. 1959, 29, 3631; 8.87 g), adding the butyllithium in hexane at −30° C. and the isoamyl nitrate at 0° C. The product 2-methyl-5-(nitromethylthio)thiophene, was obtained as an oil in 9% yield after column chromatography eluting with 10% ethyl acetate/hexane; NMR: 2.48 (s,3H), 5.38 (s,2H), 6.7 (m,1H), 7.1 (d,1H).

EXAMPLE 12

Using a similar procedure to that described in Example 9, 3-(nitromethylthio)thiophene (0.21 g) was oxidised to 3-(nitromethylsulphonyl)thiophene, obtained as a white solid (0.072 g) m.p. 74°–75° C.; NMR: 5.62 (s,2H), 7.47(2xd,1H), 7.58(2xd,1H), 8.28(dd,1H); m/e (electron impact) 207 (M$^+$); microanalysis, found: C,29.2, H,2.4, N,6.6%; C$_5$H$_5$NO$_4$S$_2$ requires: C,29.0; H,2.4, N,6.8%.

The starting material was obtained using an analogous procedure to that described for Example 9, but starting with 2-(3-thienylthio)acetic acid (described in Arkiv Khemie, 1963, 20, 297–304; 1.10 g). The product, 3-(nitromethylthio)thiophene, was obtained as an oil (32% yield) of sufficient purity for further reaction; NMR: 5.34 (s,2H), 7.14 (dd,1H), 7.4 (dd,1H), 7.54 (dd, 1H).

EXAMPLE 13

Using a modified version of the procedure described in Example 1, sodium benzo[b]thiophene-2-sulphinate (10.0 g) was converted to 2-(nitromethylsulphonyl)benzo[b]thiophene (65 mg), mp 97°–99° C.; NMR: 5.73

(s,2H), 7.58 (m,2H), 7.96 (m,2H), 8.15 (s,2H); m/e (electron impact) 257 (M+); microanalysis, found: C,42.0; H,2.8; N,5.1%; C$_9$H$_7$NO$_4$S$_2$ requires: C,42.0; H,2.7p N,5.4%; the modifications to the procedure included using ethyl acetate in the initial extractions, purifying the crude product by partition between saturated sodium bicarbonate solution and methylene chloride, acidifying (2 M hydrochloric acid) the bicarbonate phase, extracting into methylene chloride which was evaporated, and purifying the residue after chromatography by recrystallisation from ethyl acetate/hexane.

The starting material was obtained as a solid in 73% yield using an analogous procedure to that described for Example 3, starting from benzo[b]thiophene (20.0 g) and had m/e (electron impact) 197 (M+ for the sulphinate ion).

EXAMPLE 14

Using an analogous procedure to that described in Example 9, 2-(nitromethylthio)furan (1.0 g) was oxidised to 2-(nitromethylsulphonyl)furan. The oxidation was carried out for 2 hours only and after removal of the precipitated chlorobenzoic acid, the solvent was evaporated. The residue was extracted with boiling petrol 60°–80° C. (2×30 ml). Evaporation of these extracts gave an oil which was partially purified by PLC on silica gel (40×20 cm×0.5 mm plates), eluting with 25% v/v ethyl acetate/petrol 60°–80° C. The material so obtained was further purified by extraction from a chloroform solution (50 ml) into 2 M sodium hydroxide (2×25 ml) which was then acidified with 2 M hydrochloric acid and extracted with chloroform (2×30 ml). These extracts were dried (MgSO$_4$) and evaporated to give 2-(nitromethylsulphonyl)furan as an oil (105 mg); NMR: 5.70 (s,2H), 6.65 (m,1H), 7.35 (d,1H), 7.75 (s,1H); m/e (electron impact): 192 (M+); microanalysis, found C,32.0; H,2.7; N,7.4%; C$_5$H$_5$NO$_5$S requires: C,31.4; H,2.6; N,7.35%.

The starting material was obtained as follows:

A solution of 1.6 M butyllithium in hexane (93 ml) was added slowly to a solution of furan (10 g) in dry ether (385 ml). An exothermic reaction occurred and raised the temperature to 30° C. The mixture was stirred for 90 minutes and then heated under reflux for 30 minutes. Sulphur powder (4.8 g) was then added in portions over 10 minutes. The mixture was stirred for 3 hours to give a thick precipitate of the lithium salt of furan-2-thiol. The suspension was treated with a solution of sodium hydroxide (6 g) in water (200 ml) and the resulting mixture was added slowly to a solution of chloroacetic acid (14.1 g) in water (300 ml). The mixture was stirred for 3 days and then extracted with ether (2×200 ml). The extracts were discarded. The aqueous phase was acidified with 2 M hydrochloric acid and further extracted with ether (4×200 ml). These extracts were dried (MgSO$_4$) and evaporated to leave 2-(fur-2-ylthio)acetic acid (J) as a brown oil, (20.2 g); NMR (90 MHz): 3.5 (s,2H), 6.40 (m,1H), 6.55 (d,1H), 7.5 (d,1H), 8.5–9.1 (br s, 1H).

A portion of J (3.16 g) was nitrated using a similar procedure to that described for Example 9. However, in the work-up, the extracts of the acidified reaction mixture were washed only with saturated aqueous sodium bicarbonate (to remove carboxylic acid) and then with brine. There was thus obtained 2-(nitromethylthio)furan as an unstable amber oil (2.05 g) which was used without delay and had NMR (90 MHz): 5.35 (s,2H), 6.5 (m,1H), 6.8 (d,1H), 7.6 (d,1H).

EXAMPLE 15

Using a similar procedure to that described in Example 9, 5-methyl-2-(nitromethylthio)furan (2.0 g) was oxidised to 5-methyl-2-(nitromethylsulphonyl)furan, obtained as a white crystalline solid after chromatography and crystallisation from ethanol (0.52 g) mp 46°–47° C.; NMR (90 MHz): 2.45 (s,3H), 5.65 (s,2H), 6.30 (d,1H), 7.30 (d,1H), 7.30 (d,1H); m/e (electron impact) 205 (M+); microanalysis: found, C,35.1; H,3.55; N,6.5%; C$_6$H$_7$NO$_5$S requires: C,35.1; H,3.4; N,6.8%.

The necessary starting material was prepared from 2-methylfuran (16.4 g) by an analogous procedure to that described for furan itself in Example 14, except that in this case the intermediate lithium salt of 2-methylfuran-5-thiol was reacted in dry ether at −20° C. with methyl 2-chloroacetate. The reaction mixture was stirred for 2 days and then partitioned between water (800 ml) and ether (3×400 ml). The organic layers were dried (MgSO$_4$) and evaporated. The residual oil was distilled to give methyl 2-(2-methylfur-5-ylthio)acetate (40.1 g) b.p. 94°–96° C./0.5 mm; NMR (90 MHz): 2.30 (s,3H), 3.45 (s,2H), 3.70 (s,3H), 5.95 (m,1H), 6.45 (d,1H).

This ester (18.6 g) was heated under reflux in ethanol (50 ml) containing 2 M aqueous sodium hydroxide (50 ml) for one hour. The solvent was evaporated. The residual mixture was diluted with ice-water (300 ml) and extracted with ether (3×20 ml). The ice-cold aqueous layer was acidified to pH 1 with 6 M hydrochloric acid and extracted with ether (3×300 ml). These extracts were dried (MgSO$_4$) and evaporated to leave an oil which was recrystallised from petrol 60°–80° C. to give 2-(2-methylfur-5-ylthio)acetic acid, (10.1 g) m.p. 35°–36° C.; NMR (90 MHz): 2.35 (s,3H), 3.50 (s,2H), 6.00 (m,1H), 6.55 (d,1H), 11.27 (br,s).

EXAMPLE 16

A solution of 3-(nitromethylsulphonyl)indole (1.9 g, 7.9 mmol) in dry DMF (12 ml) was added slowly to a suspension of sodium hydride (0.76 g of a 55% w/w dispersion in mineral oil) in dry DMF (60 ml). The mixture was stirred until evolution of hydrogen had ceased. A solution of 4-bromo-2-fluorobenzyl bromide (2.14 g, 8 mmol) in dry DMF (12 ml) was added in one portion. The mixture was stirred for 2 hours and then poured into water. The aqueous mixture was acidified with 2 M hydrochloric acid and extracted with ethyl acetate. The combined extracts were dried (MgSO$_4$) and the solvent evaporated. The residual oil was purified by MPLC, eluting with ethyl acetate/hexane (1:4 v/v) to give 1-(4-bromo-2-fluorobenzyl)-3-(nitromethylsulphonyl)indole (0.86 g), m.p. 164°–165° C. (after recrystallisation from ethyl acetate/hexane); microanalysis, found: C,45.3; H,2.9; N,6.1%; C$_{156}$H$_{12}$BrFN$_2$O$_4$S requires: C,45.0; H,2.8; N,6.6%.

EXAMPLE 17

Using an analogous procedure to that described in Example 9, except that the oxidation was carried out for 2 hours, there was obtained 5-(nitromethylsulphonyl)-2-phenylthiophene as a white solid, m.p. 101°–102° C. (after recrystallisation from ethyl acetate/hexane); in 54% yield; NMR: 5.68(s,2H), 7.38(d,1H), 7.46(m,3H), 7.64(m,2H), 7.81(d,1H); m/e (electron impact) 283(m+); microanalysis, found: C,46.8; H,3.1; N,4.9%; C$_{11}$H$_9$NO$_4$S$_2$ requires: C,46.6; H,3.2; N,4.95%; starting from 5-(nitromethylthio)-2-phenylthiophene, itself obtained as a solid, m.p. 82°–84° C. [purified by flash chromatography (Merck Kieselgel Art. 7736) eluting with methylene chloride/hexane (1:3v/v); in 22% yield; NMR: 5.33 (s,2H), 7.21(d,1H), 7.29(d,1H), 7.39(m,3H), 7.57(dd,2H); starting from 2-(2-phenylthien-5-ylthio)acetic acid, itself obtained by the procedure described in West German OLS No. 1512272.

EXAMPLE 18

A 35% w/v solution of peracetic acid in acetic acid (3ml) was added dropwise to a stirred solution of 2-benzyl-5-(nitromethylthio)thiophene (A) (1.60 g) in chloroform (20 ml). The solution was stirred and heated at 60° C. for 2 hours, then allowed to cool and diluted with water (20 ml). The organic phase was separated, washed with a 20% w/v solution of sodium metabisulphite, and dried (MgSO$_4$). The solvent was removed by evaporation and the residue was purified by column chromatography using methylene chloride/hexane (1:1 v/v) to vie 2-benzyl-5-(nitromethylsulphonyl)thiophene as a solid (0.56 g), m.p. 61°-62° C. (after recrystallisation from ether/hexane); NMR(250 MHz): 4.40(s,2H), 5.62(s,2H), 6.95(d,1H), 7.22-7.40(m,5H), 7.68(d,H); m/e (electron impact): 297(M+); microanalysis, found: C,48.9; H,3.8; N,4.7%; $C_{12}H_{11}HO_4S$ requires: C,48.5; H,3.7; N,4.7%.

The starting thioether (A) was obtained as a yellow oil using a similar procedure to that described in Example 9; in 33% yield [after purification by column chromatography eluting with methylene chloride/hexane (1:1 v/v)]; NMR: 4.11(s,2H), 5.26(s,2H), 6.71(d,1H), 7.13(d,1H), 7.3(m,5H); m/e (chemical ionisation) 283(m+NH$_4$)+; starting from 2-(2-benzylthien-5-ylthio)acetic acid, itself obtained as described in West German OLS No. 15122272.

EXAMPLE 19

Using an analogous procedure to that described in Example 18, except that the oxidation was carried out for 4 hours, there was obtained 4-bromo-2-nitromethylsulphonyl)thiophene as a white solid, m.p. 114°-116° C. (after treatment with activated charcoal and recrystallisation from ethanol); in 68% yield; NMR: 5.67(s,2H), 7.78(dd,2H); m/e (electron impact) 285(M+); microanalysis, found: C,21.4; H,1.2; N,4.9%, $C_5H_4BrNO_4S_2$ requires: C,21.0; H,1.4; N,4.9%; starting from 4-bromo-2-(nitromethylthio)thiophene, itself obtained as an oil using a similar procedure to that described in Example 9; in 44% yield; NMR: 5.32(s,2H), 7.25(d,1H), 7.38(d,1H); starting from 2-(4-bromothien-2-ylthio)acetic acid, itself obtained as described in West German OLS No. 1612272.

EXAMPLE 20

Using a similar procedure to that described in Example 18, except that the oxidation was carried out for 24 hours, there was obtained 3-bromo-2-(nitromethylsulphonyl)thiophene as a white solid, m.p. 71°-72° C. (after recrystallisation from ether/hexane); in 60% yield; NMR: 5.82(s,2H), 7.26(d,1H); m/e(electron impact) 285(M+); microanalysis, found: C,21.4, H,1.4, N,4.8%; $C_5H_4BrNO_4S_2$ requires: C,21.0; H,1.4; N,4.9%; starting from 3-bromo-2-(nitromethylthio)thiophene, itself isolated as an oil using a similar procedure to that described in Example 9; in 43% yield [after purification by column chromatography eluting with methylene chloride/hexane (1.3v/v)]; NMR: 5.33(s,2H), 7.10(d,1H), 7.5(d,1H), m/e (chemical ionisation) 271 (M+NH$_4$)+; starting from 2-(3-bromothien-2-ylthio)acetic acid, itself obtained as follows:

A solution of 3-bromothiophene (16.3 g) in ether (25 ml) was added in portions during 20 minutes to a stirred mixture of a 1.5 M solution of lithium diisopropylamide in hexane (66.7 ml) and ether (75 ml) at −70° C. under argon. After the addition was complete, the reaction mixture was maintained at −70° C. for 2 hours. Powdered sulphur (3.2 g) was then added in small portions, and the resulting suspension was stirred for 2 hours at −70° C. The mixture was then poured into ice-water (100 ml) and the aqueous phase was separated and treated with a solution of chloroacetic acid (9.45 g) and sodium carbonate (5.8 g) in water (100 ml). The mixture was heated at 90° C. for 2 hours, then allowed to cool and extracted with ether (150 ml). The extracts were discarded. The aqueous layer was acidified to pH 2 with 2 M hydrochloric acid with ico cooling and extracted with ethyl acetate. The combined extracts were dried (MgSO$_4$) and evaporated. The residual oil was purified by flash chromatography eluting with ethyl acetate, followed by fractional recrystallisation from ethyl acetate/hexane, to give 2-(3-bromothien-2-ylthio)acetic acid as a solid, in 25% yield, m.p. 64°-65° C.; NMR: 3.56(s,2H), 7.02(d,1H), 7.45(d,1H); m/e (chemical ionisation) 270 (M+NH$_4$)+.

EXAMPLE 21

Using a similar oxidation procedure to that described in Example 9, there was obtained 2-t-butyl-5-(nitromethylsulphonyl)thiophene as an oil, in 45% yield; NMR: 1.46(s,9H), 5.63(s,2H), 7.0(d,1H), 7.68(d,1H); m/e (electron impact) 263(M+); microanalysis, found: C,41.4; H,5.0; N,5.3%; $C_9H_{13}NO_4S_2$ requires: C,41.1; H,5.0, N,5.3%; starting from 2-t-butyl-5-(nitromethylthio)thiophene, itself obtained as an oil, in 37% yield; NMR(90 MHz): 1.34(s,9H), 5.28(s,2H), 6.72(d,1H), 7.10(d,1H); starting from 2-(2-t-butylthien-5ylthio)acetic acid, itself obtained as follows:

A 1.55 M solution of butyllithium in hexane (46.1 ml) was added to a solution of 2-t-butylthiophene (10.0 g) in dry ether (50 ml) over 10 minutes. The mixture was refluxed for 45 minutes, then cooled to −70° C. and sulphur (2.27 g) was added in portions. After stirring for a further 1 hour at −70° C., the mixture was poured into water (100 ml). The aqueous phase was separated and added to a solution of chloroacetic acid (6.71 g) and potassium carbonate (4.91 g) in water (100 ml). The mixture was stirred at ambient temperature for 18 hours, then extracted with ether. The extracts were discarded. The aqueous layer was cooled in ice, acidified to PH 1 with 2 M hydrochloric acid, and extracted with ether. The extracts were combined, washed with water, and dried (MgSO$_4$). The solvent was removed by evaporation to give (2-(2-t-butylthien-5-ylthio)acetic acid as a low-melting solid, in 88% yield; NMR: 1.36(s,9H), 3.52(s,2H), 6.70(d,1H), 7.06(d,1H), 9.8(b,'H).

EXAMPLE 22

Using a similar oxidation procedure to that described in Example 9, there was obtained 2-allyl-5-(nitromethylsulphonyl)thiophene as a solid, m.p. 38°-39° C. (after recrystallisation from ether/hexane); in 33% yield; NMR: 3.66(dd,2H), 5.2(m,1H), 5.26(m,1H), 5.62(s,2H), 5.86-6.1(m,1H), 6.96(d,1H), 7.69(d,1H); m/e (electron impact)247(M+); microanalysis, found: C,38.8; H,3.6; N,5.5%; $C_8H_9NO_4S_2$ requires: C,38.9; H,3.6; N,5.7%; starting from 2-allyl-5-(nitromethylthio)thiophene, itself obtained as an oil, in 9% yield [after purification by column chromatography eluting with methylene chloride/hexane (1:3v/v)]; NMR(250 MHz): 3.55(dm,2H), 5.1–4.23(m,2H), 5.27(s,2H), 5.88–6.05(m,1H), 6.75(dd,1H), 7.17(d,1H); m/e (chemical ionisation) 233(M+NH$_4$)$^+$; starting from 2-(2-allylthien-5-ylthio)acetic acid, itself obtained as follows:

(i) A solution of thiophene (16.8 g) in dry ether (20 ml) was added during 20 minutes to a stirred 1.55 M solution of butyllithium in hexane (129 ml) at 0° C. under argon. The mixture was stirred at ambient temperature for 1 hour, then cooled to −20° C. and treated with a solution of allyl bromide (16.9 ml) in dry ether (30 ml) over 15 minutes. The mixture was heated at reflux for 18 hours, then cooled, poured onto crushed ice, and extracted with ether. The combined ether extracts were washed with water, dried (MgSO$_4$), and evaporated. The residual oil was purified by fractional distillation at reduced pressure to give 2-allylthiophene as an oil, b.p. 40°–42° C. at 6 mm Hg; in 61% yield; NMR: 3.57(dm,2H), 5.05–5.22(m,2H), 5.99(m,1H), 6.8(dd,1H), 6.93(dd,1H), 7.14(dd,1H).

(ii) A solution of 2-allylthiophene (7.15 g) in dry ether (40 ml) was added during 20 minutes to a stirred mixture of a 1.55 M solution of butyllithium in hexane (40.7 ml) and dry ether (40 ml) at ambient temperature under argon. The mixture was stirred for 2 hours at reflux, cooled to 0° C., and sulphur (2.02 g) was added in portions. The mixture was stirred for a further 15 minutes, maintaining the reaction temperature at 0° C., and then methyl 2-bromoacetate (5.8 ml) was added during 10 minutes. The mixture was stirred at ambient temperature for 18 hours, then poured onto crushed ice and extracted with ether. The combined ether extracts were washed with water, dried (MgSO$_4$), and evaporated. The residual oil was then stirred with a mixture of 2 M sodium hydroxide solution (40 ml) in ethanol (30 ml) during 1hour. The mixture was diluted with water and extracted with ether. The extracts were discarded. The aqueous layer was acidified with 2 M hydrochloric acid to pH 2 and extracted with ether. These extracts were dried (MgSO$_4$), and evaporated to give (2-(2-allylthien-5-ylthio)acetic acid as an oil, in 65% yield; NMR: 3.52(dm,2H), 5.05–5.22(m,2H), 5.8–5.1(m,1H), 6.69(dd,1H) 7.08(d,1H), 9.0(b,1H); m/e (chemical ionisation) 232 (M+NH$_4$)$^+$.

EXAMPLE 23

Using a similar oxidation procedure to that described in Example 18, there was obtained 3-methyl-2-nitromethylsulphonyl)thiophene as a white solid, m.p. 31°–32° C. (after recrystallisation from cold ethyl acetate/hexane); in 40% yield; NMR (250 MHz): 2.54(s,3H), 5.63(s,2H), 7.06; (d,1H), 7.67 (d,1H); m/e (electron impact) 221 (M$^+$); starting from 3-methyl-2-(nitromethylthio)thiophene, itself obtained as an oil using a similar procedure to that described in Example 9; in 20% yield [after purification by column chromatography eluting with methylene chloride/hexane (1:1 v/v)], NMR: 2.33(s,3H), 5.24(s,2H), 6.93(d,1H), 7.39(d,1H); m/e (chemical ionisation) 207 (M+NH$_4$)$^+$; starting from 2-(3-methylthien-2-ylthio)acetic acid, itself obtained as follows:

A solution of 2-bromo-3-methylthiophene (10.0 g) in dry ether (20 ml) was added dropwise to a stirred mixture of a 1.55 M solution of butyllithium in hexane (36.4 ml) and dry ether (80 ml) at −70° C. under argon, and the mixture was stirred at −70° C. for 1 hour. Powdered sulphur (1.79 g) was added in portions at −70° C. and the mixture was stirred for 45 minutes at this temperature. The mixture was then warmed to −60° C. and methyl 2-bromoacetate (5.2 ml) was added dropwise. The mixture was allowed to warm to ambient temperature and stirred for 18 hours, then poured onto a mixture of crushed ice (50 g) and water (100 ml). The organic layer was separated, the aqueous layer was extracted with ether, and all the organic phases were combined and dried (MgSO$_4$). The solvent was removed by evaporation, and the residual oil was dissolved in methanol (100 ml). 2 M sodium hydroxide solution (40 ml) was added, and the mixture was heated at reflux for 1 hour. Volatile material was removed by evaporation, and the residue was partitioned between water and methylene chloride. The aqueous layer was separated and acidified to pH 2 with 2 M hydrochloric acid, followed by extraction with methylene chloride. The organic extracts were dried (MgSO$_4$) and evaporated to give 2-(3-methylthien-2-ylthio)acetic acid as a low melting solid, in 65% yield; NMR (250 MHz): 2.32(s,3H), 3.45(s,2H), 6.89(d,1H), 7.31(d,1H), 7.31(d,1H); m/e (electron impact) 189(M$^+$).

EXAMPLE 24

Using a similar oxidation procedure to that described in Example 18, there was obtained 2,3,4-trichloro-5-(nitromethylsulphonyl)thiophene as a white solid, m.p. 122°–124° C. (after recrystallisation from ether/hexane); in 65% yield: NMR (250 MHz): 5.80(s,2H); m/e (chemical ionisation) 327 (M+NH$_4$)$^+$; microanalysis, found: C,19.5; H,0.7; N,4.3%; C$_5$H$_2$Cl$_3$NO$_4$S$_2$ requires: C,19.3; H,0.6; N,4.5%, starting from 2,3,4-trichloro-5-(nitromethylthio)thiophene, itself obtained as a solid, m.p. 35°–37° C. [after purification by column chromatography eluting with methylene chloride/hexane (1:3 v/v)]; in 27% yield; NMR (250 MHz): 5.34(s,2H): m/e (electron impact) 277(M$^+$); starting from 2-(2,3,4-trichlorothien-5-yl)acetic acid (A).

The acetic acid (A) was obtained as a solid, m.p. 140°–141° C; in 77% yield; NMR: 2.8–3.6(s,1H), 3.7(s,2H); 3.7(s,2H); m/e (electron impact) 276 (M$^+$); using a similar procedure to that described in Example 23 starting from tetrachlorothiophene, except that the reaction was carried out at −20° C., and that hydrolysis of the intermediate ester was performed at ambient temperature.

EXAMPLE 25

2-Bromothiophene-5-sulphonyl chloride (prepared as described in Bull. Chem. Soc. Japan, 1985,58,1063–1064)(6.5 g, 25 mmol) was added slowly to a stirred solution of sodium hydrogen carbonate (4.2 g, 50 mmol) and sodium sulphite heptahydrate (12.6 g, 50 mmol) in water (50 ml), at 70° C. The mixture was stirred at this temperature for 1.5 hours, then ice (20 g) was added, and the mixture was washed with ether (2×50 ml). The cold aqueous phase was acidified to pH 1with 2 M hydrochloric acid and extracted quickly with ether (3×50 ml). The combined extracts were dried (MgSO$_4$) and added to a solution of sodium methoxide in methanol (prepared from sodium metal (1.7 g, 75 mmol) and methanol (25 ml)). The mixture was then evaporated to dryness to give sodium 2-bromothiophene-5-sulphinate as a white solid, which was immediately dissolved in dry DMF (25 ml) and cooled to −25° C. Bromonitromethane (7.0 g, 50 mmol) was then added, the cooling bath removed, and the stirred mixture irradiated with a lamp (240 watt) for 10 minutes. Ice was then added, the mixture washed with ether (3×100 ml), and the aqueous phase acidified with 2 M hydrochloric acid. The aqueous phase was then extracted with ether (3×100 ml) and the combined extracts evaporated to give an oil which was purified by chromatography on silica gel (Merck Kieselgel Art. 7734) eluting with chloroform, to give 2-bromo-5-(nitromethylsulphonyl)thiophene as a white crystalline solid (4.2 g), m.p. 103°–104° C. (after recrystallisation from ether); in 59% yield; NMR: 5.65(s,2H), 7.25(d,2H), 7.6(d,2H); m/e (electron impact) 287(M+); microanalysis, found: C,21.2; H,1.5; N,4.8%; $C_5H_4BrNO_4S_2$ requires: C,21.0; H,1.4; N,4.9%.

EXAMPLES 26–28

Using a similar procedure to that described in Example 25, but starting from the appropriately substituted sulphonyl chloride of the formula $Q.SO_2Cl$, the following compounds at the formula I were obtained as solids:

EXAMPLE 26

2,3-dibromo-5-(nitromethylsulphonyl)thiophene, m.p. 108°–111° C. (after recrystallisation from ether/hexane); in 2% yield; NMR: 5.65(s,2H), 7.66(s,1H); m/e (electron impact) 363(M+); microanalysis, found: C,16.8; H,1.0; N,3.9%; $C_5H_3Br_2NO_4S_2$ requires: C,16.5; H,0.8; N,3.8%;

EXAMPLE 27

2-methyl-3-(nitromethylsulphonyl)benzo[b]thiophene, m.p. 92°–93° C. (after recrystallisation from ethyl acetate/hexane); in 0.8% yield; NMR: 2.9(s,3H), 5.65(s,2H), 7.5(m,2H), 7.85(m,1H), 8.15(m,1H); m/e (electron impact) 271(M+); microanalysis, found: C,44.3; H,3.4; N,5.1%; $C_{10}H_9NO_4S_2$ requires: C,44.3; H,3.3; N,5.2%.

EXAMPLE 28

2-iodo-5-(nitromethylsulphonyl)thiophene, m.p. 140°–141° C. (after recrystallisation from ethanol); in 30% yield; NMR: 6.01(s,2H), 7.42(d,1H), 7.50(d,1H); m/e (chemical ionisation) 351 (M+MH$_4$)+, 333(M+); microanalysis, found: C,18.2; H,1.2; N,4.2%; $C_5H_4INO_4S_2$ requires: C,18.0;p H,1.2; N,4.2%.

The starting sulphonyl chlorides of the formula $Q.SO_2Cl$ used in Examples 27 and 28 were obtained as follows:

2-metylbenzo[b]thiophene-3-sulphonyl chloride was obtained as described in U.S. Pat. No. 4,391,627, starting from 2-methylbenzo[b]thiophene, itself obtained as described in *J. Am. Chem. Soc.*, 1952, 74, 664. 2-Iodothiophene-5-sulphonyl chloride was obtained as described in *Bull. Chem. Soc. Japan*, 1985, 58, 1063–1064.

EXAMPLES 29–30

Using a similar procedure to that described in Example 25, but starting from the appropriately substituted sodium sulphinate salt of the formula $A.SO_2^-Na^+$ in place of sodium 2-bromothiophene-5-sulphinate, the following compounds of the formula I were obtained:

EXAMPLE 29

7-methyl-2-(nitromethylsulphonyl)benzo[b]thiophene, m.p. 102°–103° C. (after recrystallisation from ether/hexane); in 1.5% yield*; NMR: 2.6(s,3H), 5.75(s,2H), 7.456(m,2H), 7.85(m,1H), 8.15(s,1H); m/e (electron impact) 271(M+); microanalysis, found: C,44.1; H,2.9; N,4.8%; $C_{10}H_9NO_4S_2$ requires: C,44.3; H,3.3; N,5.2%; [ * The reaction was carried out using 1,3-dimethyl-3,4,5,6-tetrahydro-2(1H)-pyrimidinone as solvent in place of DMF].

EXAMPLE 30

5-methyl-2-(nitromethylsulphonyl)benzo[b]thiophene, m.p. 96°–97° C. (after recrystallisation from aqueous ethanol); in 2.6% yield; NMR: 2.5(s,3H), 5.7(s,2H), 7.45(m,1H), 7.75(s,1H), 7.8(d,1H), 8.05(s,1H); m/e (electron impact) 271(M+); microanalysis, found: C,44.4; H,3.3; N,4.9%; $C_{10}H_9NO_4S_2$ requires: C,44.3; H,3.3; N,5.2%.

The starting sodium sulphinate salts of the formula $Q.SO_2^-Na^+$ used in Examples 29 and 30 were obtained using an analogous procedure to that described in Example 3, starting from 7-metylbenzo[b]thiophene (prepared as described in *J. Chem. Soc.*, 1964,981) and 5-methylbenzo[b]thiophene respectively.

EXAMPLE 31

Using an analogous procedure to that described in Example 1 but starting from sodium benzo[b]thiophene-3-sulphinate (1.1 g), there was obtained 3-(nitromethylsulphonyl)benzo[b]thiophene as a solid (20 mg), m.p. 72°–73° C. (after recrystallisation from ether/hexane); NMR: 7.6(m,2H), 8.0(m,1H), 8.2(m,1H); m/e (electron impact) 276(M+); microanalysis, found: C,41.9; H,2.7; N,5.4%; $C_9H_7NO_4S_2$ requires: C,42.0; H,2.7; N,5.4%.

The starting sulphinate salt was prepared as described in Example 1, starting from benzo[b]thiophene-3-sulphonyl chloride, itself obtained as described in U.S. Pat. No. 4,391,627, in 63% yield.

EXAMPLE 32

Using a similar oxidation procedure to that described in Example 9, but starting from 4-methyl-2-(nitromethylsulphinyl) thiophene(A) in place of 2-methoxy-5-(nitromethylthio)thiophene, there was obtained 4-methyl-2-(nitromethylsulphonyl)thiophene as a white solid, m.p. 71°–72° (after recrystallisation from aqueous ethanol); in 84% yield; NMR (400 MHz); 2.34(s,3H), 5.63(s,2H), 7.49(d,1H), 7.63(d,1H); m/e (electron impact) 221(M+); microanalysis, found: C,32.6; H,3.1; N,6.2%; $C_6H_7NO_4S_2$ requires: C,32.6; H,3.17; N,6.33%.

The starting material (A) was obtained as follows:

(i) 3-Methylthiophene (15 g) in dry ether (50 ml) was added slowly to a stirred mixture of a 1.6 M solution of butyllithium in hexane (95.7 ml) and ether (200 ml) under argon. After stirring for 90 minutes, the mixture was refluxed for 30 minutes, and then cooled to below 5° C. Powdered sulphur (4.9 g) was added in portions keeping the temperature below 10° C. The solution was stirred for 30 minutes at ambient temperature and then with ice-cooling treated with methyl 2-bromoacetate (14.2 ml). After stirring for 18 hours, the mixture was poured into water (300 ml), the ether layer separated, and the aqueous layer further extracted with ether (200 ml). The combined ether layers were dried (MgSO$_4$) and evaporated, and the resultant oil was dissolved in methanol (80 ml), and 2 M sodium hydroxide solution (76.5 ml) was added. The mixture was stirred for 1 hour, then acidified with 2 M hydrochloric acid, and poured into water (100 ml). The mixture was extracted with ether (2×300 ml) and the combined extracts washed with saturated sodium hydrogen carbonate solution. The basic aqueous washings were acidified with 2 M hydrochloric acid and extracted with ether (2×200 ml).

These combined extracts were dried (MgSO$_4$) and evaporated, to give 2-(4-methylthien-2-ylthio)acetic acid (B) as an oil (10.2 g, 36% yield); NMR: 2.23(s,3H), 3.53(s,2H), 6.96(d,1H), 7.05(d,1H); containing approximately 15% of 2-(3-methylthien-2-ylthio)acetic acid; and which was used without further purification.

(ii) Using a similar nitration procedure to that described in Example 9, but using isobutyl nitrate in place of isoamyl nitrate, the thioacetic acid B was converted to 4-methyl-2-(nitromethylthio)thiophene (C), which was obtained as an oil (34% yield); NMR (400 MHz): 2.24(s,3H), 5.3(s,2H), 7.07 (dd,1H), 7.12(d,1H); containing approximately 15% of 3-methyl-2-(nitromethylthio)thiophene; and which was used without further purification.

(iii) Using a similar oxidation procedure to that described in Example 9, except that the reaction was carried out for 3 hours at ambient temperature followed by 3hours at reflux, the thioether (C) was converted to 4-methyl-2-(nitromethylsulphinyl)thiophene (A), which was obtained as a solid, m.p. 73°–75° C. [after recrystallisation from ethanol/water (2:1 v/v)]; NMR (250 MHz): 2.34(bs,3H), 5.38–5.64(m,2H), 7.38(dd,1H), 7.42(d,1H); m/e (chemical ionisation) 223 (M+NH$_4$)$^+$; microanalysis, found: C,35.3; H,3.5; N,6.7; C$_6$H$_7$NO$_3$S$_2$ requires: C,35.1; H,3.4; N,6.8%.

EXAMPLE 33

Using an analogous oxidation procedure to that described in Example 9, there was obtained 2-methoxymethyl-5-(nitromethylsulphonyl)-thiophene as a white solid, m.p. 50°–51° C. (after recrystallisation from aqueous ethanol); in 19% yield; NMR: 3.47(s,3H), 4.67(bs,2H), 5.63(s,2H), 7.08(dd,1H), 7.73(d,1H); m/e (chemical ionisation) 269 (M+NH$_4$)$^+$; microanalysis, found: C,33.7; H,3.6; N,5.5%; C$_7$H$_9$NO$_5$S$_2$ requires: C,33.5; H,3.6; N,5.5%; starting from 2-methoxymethyl-5-(nitromethylthio)thiophene, itself obtained as an oil, using a similar nitration procedure to that described in Example 9 but using isobutyl nitrate in place of isoamyl nitrate; in 12% yield; NMR: 3.38(s,3H), 4.56(bs,2H), 5.3(s,2H), 6.92(dd,2H), 7.2(d,2H); starting from 2-(2-methoxymethylthien-5-ylthio)acetic acid, itself obtained as follows:

(i) A solution of 2-hydroxymethylthiophene (19.7 g) in DMF (40 ml) was added to a suspension of hexane-washed sodium hydride (7.6 g of a 60% w/w dispersion in paraffin oil) in DMF (80 ml) maintaining the temperature below 30° C. The mixture was stirred for 90 minutes and then iodomethane (10.8 ml) was added slowly with ice-cooling. After stirring for 2 hours the mixture was poured into water (100 ml) and extracted with ether (2×200 ml). The combined extracts were washed with water (3×100 ml), dried (MgSO$_4$), and evaporated to give crude 2-methoxymethylthiophene as an oil (18 g, 81.4%); NMR: 3.37(s,3H), 4.61(s,2H), 6.99(m,2H), 7.28(m,1H); m/e (electron impact) 128(M$^+$).

(ii) Using a similar procedure to that described in Example 32, part (i), 2-methoxymethylthiophene (10.09 g) was lithiated and reacted with sulphur at 25°–30° C. After stirring the reaction mixture for 2 hours, the mixture was poured into water (150 ml) and the aqueous layer separated. A solution of potassium carbonate (5.45 g) and chloroacetic acid (7.45 g) in water (25 ml) was added to the aqueous layer, and the mixture allowed to stand for 18 hours. The mixture was acidified to pH 2 with 2 M hydrochloric acid and extracted with ether (2×150 ml). The organic extracts were combined, dried (MgSO$_4$), treated with activated carbon, and evaporated, to give 2-(2-methoxymethylthien-5-ylthio)acetic acid as a viscous brown oil (3.1 g, 18% yield); NMR: 3.26(s,2H), 3.6(s,2H), 4.52(s,2H), 6.95(d,1H), 7.09(d,1H); m/e (chemical ionisation) 236 (M+NH$_4$)$^+$.

EXAMPLE 34

Using an analogous procedure to that described in Example 9, except that the oxidation was carried out at 0° C. and the reaction mixture was then maintained at −18° C. for 2 days, there was obtained 3-(4-methylphenoxy)-2-(nitromethylsulphonyl)thiophene as a solid, m.p. 88°–89° C. (after recrystallisation from ether); in 15% yield; NMR: 2.35(s,3H), 5.80(s,2H), 6.60(d,1H), 7.1(q,4H), 7.65(d,1H); m/e (electron impact) 313 (M$^+$); microanalysis, found: C,46.2; H,3.5; N,4.6%; C$_{12}$H$_{11}$NO$_5$S$_2$ requires: C,46.0; H,3.5; N,4.5%; starting from 3-(4-methylphenoxy)-2-(nitromethylthio)thiophene, itself obtained as an oil [after purification by preparative thin layer chromatography on silica gel plates eluting with ethyl acetate/petrol 60°–80° C. (1:1 v/v)]; NMR: 2.35(s,3H), 5.25(s,2H), 6.65(d,1H), 7.0(q,4H), 7.37(d,1H); m/e (chemical ionisation) 299 (M+NH$_4$)$^+$,282(M$^+$); starting from 2-[3-(4-methylphenoxy)thien-5-ylthio]acetic acid, which was obtained as follows:

A 1.5 M solution of butyllithium in hexane (13.2 ml) was added dropwise to a stirred solution of 3-(4-methylphenoxy)thiophene (3.8 g, 20 mmol) (obtained as described in J.O.C., 1982, 47, 1756) in dry ether (40 ml) at −70° C. under an atmosphere of argon. The mixture was allowed to warm to ambient temperature, and then stirred for 4 hours. The reaction mixture was re-cooled to −70° C., and powdered sulphur (0.64 g, 20 mmol) was added in portions. When the addition was complete, the reaction mixture was stirred at −10° C. for 2hours, and then a solution of chloroacetic acid (0.94 g) and potassium carbonate (1.58 g) in water (15 ml) was slowly added. The mixture was stirred for 2 hours at ambient temperature, and then the organic phase was removed, and the aqueous phase stirred for a further 17 hours. The aqueous phase was washed with ether (30 ml), treated with ice, and then acidified to pH 2 with 2 M hydrochloric acid and extracted with ether (3×50 ml). The combined extracts were dried (MgSO$_4$), and the solvent removed by evaporation to give an oil, which was purified by column chromatography (Merck Kieselgel Art 7734) eluting with ethyl acetate/petrol 60°–80° (1:1 v/v), to give 2-[3-(4-methylphenoxy)thien-5-ylthio]acetic acid, as an oil (0.52 g, 9.2% yield); NMR: 2.23(s,3H), 3.30(s,2H), 6.55(d,1H), 6.9(q,4H), 7.15(d,1H).

EXAMPLE 35

A 35% w/v solution of peracetic acid in acetic acid (5 ml) was added to a solution of 2-(4-chlorophenyl)-5-(nitromethylthio)furan (A) (1.1 g, 3.7 mmol) in chloroform (20 ml), and allowed to stand for 17 hours. The reaction mixture was poured into saturated sodium chloride solution (20 ml), and extracted with chloroform (3×20 ml). The combined extracts were dried (MgSO$_4$), and the solvent removed by evaporation. The resultant residue was purified by preparative thin layer chromatography eluting with ethyl acetate/petrol 60°–80° (1:3 v/v), to give 2-(4-chlorophenyl)-5-(nitromethylsulphonyl)furan as a white solid (0.074 g), m.p. 146° C. (after recrystallisation from ether); NMR: 5.70(s, 2H), 6.85(d,1H), 7.45(d, 1H), 7.60(q, 4H); m/e (chemical ionisation): 319 (M+NH$_4$)+, 301 (M+); microanalysis, found: C,44.0; H,2.6; N,4.5%; C$_{11}$H$_8$ClNO$_5$S requires: C,43.8; H,2.7; N,4.6%.

The starting thioether (A) was obtained by an analogous nitration procedure to that described in Example 9, starting from 2-(2-(4-chlorophenyl)fur-5-ylthio)acetic acid, itself obtained by an analogous procedure to that described in Example 34, starting from 2-(4-chlorophenyl)furan, which was prepared by the procedure described in *J. Chem. Soc.,* 1946, 895.

EXAMPLE 36

Using a similar oxidation procedure to that described in Example 5, but starting from 3-methyl-7-(nitromethylsulphinyl)benzo[b]thiophene (A) (1.12 g, 4.39 mmol) and potassium permanganate (0.47 g, 2.97 mmol) at ambient temperature, there was obtained 3-methyl-7-(nitromethylsulphonyl)benzo[b]thiophene as a yellow solid (215 mg), m.p. 115°-116.5° C. (after purification by flash chromatography using dichloromethane/hexane (4:1 v/v) followed by crystallisation from isopropanol): NMR: 2.55(s, 3H), 5.7(s, 2H), 7.3(s, 1H), 7.6-8.1(m, 3H); m/e (electron impact) 271 (M+); microanalysis, found: C,44.4; H,3.4; N,4.8%; C$_{10}$H$_9$NO$_4$S$_2$ requires: C,44.3; H,3.4; N,5.2%.

The starting material (A) was obtained as follows:

(i) Using a similar procedure to that described in part (i) of Example 6, except that acetone (125 ml) was used as a co-solvent in the stirred mixture of basic copper carbonate and thioglycolic acid, 7-amino-3-methylbenzo[b]thiophene (prepared as described in JCS Perkin Trans I. 1972, 1401) (23.7 g, 145 mmol) was converted to 2-(3-methylbenzo[b]thien-7-ylthio)acetic acid, which was obtained as an orange solid (5.1g) (after flash chromatography using 9:1 v/v dichloromethane/ethyl acetate followed by crystallisation from cyclohexane), and was used without further purification or characterisation.

(ii) Using a similar procedure to that described in part (ii) of Example 4, 2-(3-methylbenzo[b]thien-7-ylthio)acetic acid (5 g, 21 mmol) was converted to 3-methyl-7-(nitromethylthio)benzo[b]thiophene, which was obtained as a yellow oil which solidified on standing (1.6 g) (after flash chromatography using 4:1 v/v hexane/ether as eluant); NMR: 2.45(s, 3H), 5.7(s, 2H), 7.15(s, 1H), 7.35-7.8(m, 3H).

(iii) A solution of potassium peroxymonosulphate ('oxane' trade mark; 1.0 g, 1.63 mmol) in water (20 ml) was added in one portion to a stirred solution of 3-methyl-7-(nitromethylthio)benzo[b]thiophene (0.7 g, 2.93 mmol) in 1,2-dimethoxyethane (40 ml) cooled to 5° C. The mixture was allowed to warm to ambient temperature and stirred for 18 hours. The reaction mixture was diluted with water (50 ml) and extracted with ethyl acetate (3×50 ml). These extracts were washed with water, dried (MgSO$_4$), and evaporated to leave an oil, which was purified by flash chromatography using 4:1 v/v dichloromethane/hexane as eluant, to give 3-methyl-7-(nitromethylsulphinyl)benzo[b]thiophene as a pale yellow solid (0.35 g); NMR:2.5(s, 3H), 5.55(s, 2H), 7.25(s, 1H), 7.6-8.0(m, 3H).

EXAMPLE 37

Using a similar oxidation procedure to that described in Example 9, there was obtained 2-t-butoxy-5-(nitromethylsulphonyl)thiophene as a pale brown oil, in 24.3% yield; NMR: 1.48(s, 9H), 5.6(s, 2H), 6.46(d, 1H), 7.58(d, 1H); m/e (chemical ionisation) 297(M+NH$_4$)+; microanalysis, found: C,38.8; H,4.7; N,5.4%; C$_9$H$_{13}$NO$_5$S$_2$ requires: C,38.7; H,4.66; N,5.02%; starting from 2-t-butoxy-5-(nitromethylthio)thiophene, itself obtained as an oil, using a similar nitration procedure to that described in Example 9 but using isobutyl nitrate in place of isoamyl nitrate; in 32% yield; NMR (250 MHz): 1.4(s, 9H), 528(s, 2H), 6.3(d, 1H), 7.05(d, 1H); m/e (chemical ionisation) 265 (M+NH$_4$)+; starting from 2-(2-t-butoxythien-5-ylthio)acetic acid, itself obtained as follows:

(i) An ethereal solution of 2-thiophenemagnesium bromide was prepared by the addition of a solution of 2-iodothiophene (50 g) in ether (200 ml) over 1 hour to a stirred suspension of magnesium turnings (6.37 g) in ether (75 ml) containing a crystal of iodine, and maintaining gentle reflux throughout. After stirring 2hours at ambient temperature, the mixture was treated slowly at 0°-5° C. with a solution of t-butyl perbenzoate (50.8 g) in ether (100 ml). The reaction mixture was maintained at 0°-5° C. for 2 hours and then allowed to stir an ambient temperature for 18 hours. The reaction mixture was poured into a mixture of ice-water (300 ml) and 2 M hydrochloric acid (50 ml) and the organic phase separated. The aqueous phase was extracted with ether (2×400 ml) and all organic phases were combined, washed with 2 M sodium hydroxide solution and dried (MGSO$_4$). The solvent was removed by evaporation to give an oil, which was purified by chromatography on silica gel to give 2-t-butoxythiophene (20.1 g, 54.1% yield); NMR (250 MHz): 1.38(s, 9H), 6.4(m, 1H), 6.75(m, 2H); m/e (chemical ionisation) 157 (M+H)+.

(ii) Using a similar procedure to that described in part (ii) of Example 33, except that the addition of sulphur was carried out at −70° C., 2-t-butoxythiophene was converted to 2-(2-t-butoxythien-5-ylthio)acetic acid, which was obtained as a viscous dark oil (14.5 g, 48% yield); NMR (DMSOd$_6$): 1.32(s, 9H), 3.5(s, 2H), 6.33(d, 1H), 6.95(d, 1H); m/e (chemical ionisation) 264 (M+NH$_4$)+.

EXAMPLE 38

2,3-Dichloro-5,6-dicyano-1,4-benzoquinone (1.88 g, 8.3 mmol) was added to a suspension of 5-(nitromethylsulphonyl)indoline (1.33 g, 5.5 mmol) in xylene (50 ml), and the mixture was stirred at reflux for 4 hours. The solvent was removed by evaporation and the residue was purified by flash chromatography on silica (Merck Kieselgel Art. 7736) eluting with ethyl acetate/toluene (1:1 v/v) to give 5-nitromethylsulphonyl)indole as a reddish solid, m.p. 117° C. (after recrystallisation from ethanol), in 47% yield; microanalysis, found: C,45.1; H,3.3; N,11.5%; C$_9$H$_8$N$_2$O$_4$S requires: C,45.0; H,3.3; N,11.7%.

5-(nitromethylsulphonyl)indoline was obtained as follows:

(i) Using a similar procedure to that described in Example 1, there was obtained 1-acetyl-5-(nitromethylsulphonyl)indoline as a pale yellow solid, m.p. 210° C.; microanalysis, found: C,46.5; H,4.3; N,9.6%; C$_{11}$H$_{12}$N$_2$O$_5$S requires: C,46.5; H,4.2; N,9.8%; starting from 1-acetyl-5-indolinesulphonyl chloride, itself obtained by the procedure described in Zhur. Obs. Khim. 1960, 30(4), 1218-1222.

(ii) 1-Acetyl-5-(nitromethylsulphonyl)indoline (5.41 g, 19 mmol) was added in one portion to a boiling mixture of 2 M hydrochloric acid (60 ml) and ethanol (20 ml). The mixture was heated at reflux until a clear solution formed, and then for a further 5 minutes. The hot reaction mixture was poured into ice-cold saturated sodium hydrogen carbonate solution (100 ml) and then extracted with ethyl acetate. The combined extracts were dried (MgSO$_4$) and the solvent was removed by evaporation. The resultant yellow oil was purified by flash chromatography on silica (Merck kieselgel Art. 7736), eluting with dichloromethane, to give 5-(nitromethylsulphonyl)indoline as a pale yellow solid, m.p. 139° C.; microanalysis, found: C,44.5; H,4.1; N,11.4%; C$_9$H$_{10}$N$_2$O$_4$S requires: C,44.6; H,4.1; N,11.6%.

EXAMPLE 39

Using a similar procedure to that described in Example 38, but starting from 1-ethyl-5-(nitromethylsulphonyl)indoline, there was obtained 1-ethyl-5-(nitromethylsulphonyl)indole as a white solid, m.p. 125° C. (after purification by flash chromatography eluting with dichloromethane, followed by recrystallisation from ethanol); microanalysis, found: C,49.6; H,4.5; N,10.5%; C$_{11}$H$_{12}$N$_2$O$_4$S requires: C,49.3; H,4.5; N,10.5%.

1-ethyl-5-(nitromethylsulphonyl)indoline was obtained as follows:

Tetrabutylammonium borohydride (3.85 g, 15 mmol) was added to a solution of 1-acetyl-5-(nitromethylsulphonyl)indoline (1.45 g, 5 mmol) in dichloromethane (30 ml), and the mixture was stirred at reflux for 18 hours. The solvent was removed by evaporation, 2 M hydrochloric acid (30 ml) was added, and the mixture was heated at reflux for 20 minutes. The solution was then poured into sufficient of an ice-cold saturated solution of sodium hydrogen carbonate to adjust the mixture to pH 6. The mixture was then extracted with dichloromethane, the combined extracts were dried (MgSO$_4$), and the solvent was removed by evaporation. The resultant yellow oil was purified by flash chromatography on silica (Merck kieselgel Art. 7736), eluting with dichloromethane, to give 1-ethyl-5-(nitromethylsulphonyl)indoline as a solid, m.p. 122° C.; microanalysis, found: C,49.3; H,5.1; N,10.4%; C$_{11}$H$_{14}$N$_2$O$_4$S requires: C,48.9; H,5.2; N,10.4%.

EXAMPLE 40

A mixture of 2-t-butyl-5,5-dimethyl-2-[2-(nitromethylsulphonyl)thien-5-yl]-1,3-dioxane (A) (1.47 g), trifluoroacetic acid (15 ml), and water (1.5 ml) was stirred for 45 minutes at 60° C. The reaction mixture was poured into water (50 ml), and extracted with ether (2×50 ml). The combined ether extracts were washed with saturated aqueous sodium hydrogen carbonate solution (20 ml), water (3×20 ml), and then dried (MgSO$_4$). The solvent was removed by evaporation to give 2-(2,2-dimethylpropionyl)-5-(nitromethylsulphonyl)thiophene as a white solid (0.605 g, 54% yield), m.p. 98°-99° C. (after recrystallisation from aqueous ethanol); MMR (250 MHz): 1.42(s, 9H), 5.72(s, 2H), 7.78(d, 1H), 7.82(d, 1H); m/e (electron impact) 292 (M+H)$^+$; microanalysis, found: C,41.3, H,4.5, N,4.7%; C$_{10}$H$_{13}$NO$_5$S$_2$ requires: C,41.2, H,4.5, N,4.8%.

The starting material (A) was obtained as follows:

(i) A mixture of 2-(2,2-dimethylpropionyl)thiophene (21.45 g), 2,2-dimethylpropane-1,3-diol (14.63 g), and a catalytic amount of p-toluenesulphonic acid in benzene (100 ml) was heated at reflux for 44 hours using a Dean and Stark apparatus. The mixture was cooled, diluted with ether (150 ml), and washed with saturated aqueous sodium hydrogen carbonate solution. The organic phase was then dried (MgSO$_4$) and decolourised with activated charcoal. The solvent was removed by evaporation to give 2-t-butyl-5,5-dimethyl-2-(thien-2-yl)-1,3-dioxane (B) as a white solid (31.9 g, 98% yield); NMR: 0.57(s, 3H), 1.0(s, 9H), 1.21(s, 3H), 3.36(m, 2H), 3.62(d, 2H), 6.9(dd, 1H), 7.01(dd, 1H), 7.3(dd, 1H); mass spectrum (chemical ionisation) 255 (M+H)$^+$.

(ii) Using a similar procedure to that described in part (ii) of Example 33, but acidifying the reaction mixture to pH 4 with 10% aqueous citric acid instead of 2 M hydrochloric acid, the thiophene (B) was converted to 2-[2-(2-t-butyl-5,5-dimethyl-1,3-dioxan-2-yl)thien-5-ylthio]acetic acid (C), which was obtained as a viscous red oil (7.2 g, 50.4% yield); NMR: 0.59(s, 3H), 0.97(s, 9H), 1.19(s, 3H), 3.39(d, 2H), 3.55(s, 2H), 3.6(d, 2H), 6.77(d, 1H), 7.13(d, 1H); m/e (chemical ionisation) 345 (M+H)$^+$.

(iii) Using a similar nitration procedure to that described in Example 9, but starring from acid (C) and using isobutyl nitrate in place of isoamyl nitrate, there was obtained 2-t-butyl-5,5-dimethyl- 2-[2-(nitromethylthio)thien-5-yl]-1,3-dioxane (D) as an oil, in 47% yield; NMR: 0.6(s, 3H), 0.96(s, 9H), 1.2(s, 3H), 3.36(dd, 2H), 3.55(d, 2H), 5.32(s, 2H), 6.82(d, 1H), 7.22(d, 1H); m/e (chemical ionisation) 346 (M+H)$^+$.

(iv) Using a similar oxidation procedure to that described in Example 9, but starring from the thioether (D), there was obtained 2-t-butyl-5,5-dimethyl-2-[2-(nitromethylsulphonyl)thien-5-yl]-1,3-dioxane (A) as a white solid, m.p. 88°-89° C. (without recrystallisation); in 70% yield; NMR: 1.0(s, 9H), 1.22(s, 3H), 3.48(m, 4H), 5.66(s, 2H), 7.03(d, 1H), 7.76(d, 1H); m/e (chemical ionisation) 395 (M+NH$_4$)$^+$.

EXAMPLE 41

Using an analogous procedure to that described in Example 18, there was obtained 5-cyano-2-(nitromethylsulphonyl)thiophene as a solid, m.p. 97°-98° C. (after recrystallisation from aqueous ethanol); in 14% yield; NMR: 5.72(s, 2H), 7.77(q, 2H); m/e (electron impact) 233 (M+H)$^+$; microanalysis, found: C,31.0; H,1.8; N,11.8%; C$_6$H$_4$N$_2$O$_4$S$_2$ requires; C,31.0; H,1.7; N,12.1%; starting from 5-cyano-2-(nitromethylthio)thiophene, itself obtained as follows:

A 1.6 M solution of butyllithium in hexane (19.0 ml. 28 mmol) was added to a stirred solution of diisopropylamine (3.9 ml, 28 mmol) in dry ether (40 ml) at −70° C. under argon, and the resulting solution was stirred at −70° C. for 45 minutes. A solution of 2-cyanothiophene (2.6 ml, 28 mmol) in dry ether (10 ml) was then added. The mixture was stirred at −70° C, for 1 hour, then sulphur (1.27 g, 28 mmol) was added slowly at −50° C. After stirring the mixture at −50° C. for 1 hour, it was allowed to warm to ambient temperature and then stirred for a further 30 minutes. The resultant mixture, containing the lithium salt of 5-cyanothiophene-2-thiol, was diluted with ether (100 ml) and a solution of sodium hydroxide (1.68 g, 42 mmol) in water (100 ml) was added. Nitromethane (1.54 ml, 28 mmol) was then added to the vigorously stirred mixture followed by powdered potassium ferricyanide (9.34 g, 56 mmol), and the resultant mixture was stirred at ambient temperature for 1 hour. The mixture was filtered through diatomaceous earth to remove insoluble matter and the aqueous phase was separated and acidified to pH 1with 28% hydrochloric acid. The mixture was extracted with ethyl acetate, dried (MgSO$_4$), and the solvent was removed by evaporation. The resultant oil (2.6 g) was purified by flash chromatography (Merck Kieselgel Art 9385) using ethyl acetate/hexane (1:4 v/v), to give 5- cyano-2-(nitromethylthio)thiophene as an oil (0.5 g, 10% yield); NMR: 5.4(s,2H), 7.4(q,2H).

EXAMPLE 42

Using a similar procedure to that described in Example 25, but starting from 2,3-dichlorothiophene-5-sulphonyl chloride, there was obtained 2,3-dichloro-5-(nitromethylsulphonyl)thiophene as a white solid, m.p. 77°–79° C. (after recrystallisation from ether/hexane); in 2% yield; NMR: 5.66(S,2H), 7.67(S,1H); m/e (electron impact) 275(M+); microanalysis, found: C,21.5; H,1.2; N,4.8%; $C_5H_3Cl_2NO_4S_2$ requires: C,21.8p; H,1.1; N,5.1%.

EXAMPLE 43

Using a similar procedure to that described in Example 25, but starting from sodium 2-(4-bromo-2-fluorobenzyl)thiophene-5-sulphinate, there was obtained 2-(4-bromo-2-fluorobenzyl)-5-(nitromethylsulphonyl) thiophene as a solid, m.p. 84°–85° C. (after recrystallisation from ether/hexane); in 3% yield; NMR: 4.20(s,2H), 5.60(s,2H), 6.95(d,1H), 7.10(t,1H), 7.26–7.31(m,2H), 7.68(d, 1H); m/e (electron impact) 393 (M+); microanalysis, found: C,36.4; H,2.3; N,3.4%; $C_{12}H_9BrFNO_4S_2$ requires: C,36.5; H,2.3; N,3.5%.

The starting sodium sulphate salt was obtained as follows:

(i) Using a similar procedure to that described in Example 22, part (i), but starting from 4-bromo-2-fluorobenzyl bromide in place of allyl bromide and carrying out the reaction at 30° C., there was obtained (4-bromo-2-fluorobenzyl)thiophene as an oil, b.p. 117°–120 C. at 0.7 mm Hg.* ; in 39% yield; NMR: 4.12(s,2H), 6.80(dd,1H), 6.88–6.96(m,1H), 7.02–7.3(m,4H); m/e (electron impact) 270 (M+); [* unreacted 4-bromo-2-fluorobenzyl bromide was removed by quaternisation with triethylamine prior to distillation of the product].

(ii) A solution of bromine (0.44 ml) in acetic acid (5 ml) was added during 10 minutes to a stirred solution of (4-bromo-2-fluorobenzyl)thiophene (2.33 g) in acetic acid (10 ml). The solution was stirred for 2 hours, then poured into a mixture of water (50 ml) and a 20% w/v solution of sodium metabisulphite (20 ml). The mixture was extracted with ether (2×50 ml), the combined extracts washed with water and saturated brine, and then dried (MgSO4). The solvent was removed by evaporation to give 2-bromo-5-(4-bromo-2-fluorobenzyl)thiophene as an oil; in 72% yield; NMR: 4.04(s,2H), 6.55(d,1H), 6.85(d,1H), 7.07(t,1H), 7.14–7.30(m,2H); m/e, (chemical ionisation) 348(M+); which was used without further purification.

(iii) A 1.6 M solution of butyllithium in hexane (3.75 ml) was added during 10 minutes to a stirred solution of 2-bromo-5-(4-bromo-2-fluoro benzyl)thiophene (2.1 g) in dry ether (50 ml) at −70° C. under argon. The mixture was stirred at −70° C. for 1 hour, then warmed to −30° C. and treated with gaseous sulphur dioxide (3 g). The mixture was stirred at −30° C. for 30 minutes, then warmed to ambient temperature and poured into water (50 ml). The organic layer was separated, dried (MgSO4) and evaporated to leave an oil (1.64 g). The oil was dissolved in ethanol (20 ml) and a solution of sodium ethoxide in ethanol (21% w/v, 1.2 ml), was added. The mixture was evaporated to dryness and the residue was triturated with ether (20 ml) to give sodium 2-(4-bromo-2-fluorobenzyl) thiophene-5-sulphinate as a solid; in 40% yield; NMR(DMSOd6): 4.06(s,2H), 6.65(d,1H), 6.71(d,1H), 7.20–7.55(m,3H); m/e (positive fast atom bombardment) (M+Na)+379; which was used without further purification.

EXAMPLE 44

The following illustrate representative pharmaceutical dosage forms containing the compound of formula I, or a non-toxic salt thereof (hereafter compound Z), for therapeutic or prophylactic use in humans:

| (a) Tablet I | mg/tablet |
|---|---|
| Compound Z | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | mg/tablet |
| Compound Z | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound Z | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound Z | 10 |
| Lactose Ph.Eur | 488.5 |
| Magnesium stearate | 1.5 |
| (e) Injection I (50 mg/ml) | |
| Compound Z | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |
| (f) Injection II (10 mg/ml) | |
| Compound Z | 1.0% w/v |
| Sodium phosphate EP | 3.6% w/v |
| 0.1M Sodium hydroxide solution | 15.0% v/v |
| Water for injection to 100% | |
| (g) Injection III (1 mg/ml, buffered to pH6) | |
| Compound Z | 0.1% w/v |
| Sodium phosphate BP | 2.26% w/v |
| Citric acid | 0.38% w/v |
| Polyethylene glycol 400 | 3.5% w/v |
| Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

|   | CHEMICAL FORMULAE |
|---|---|
| I | $Q.SO_2.CH_2.NO_2$ |
| II | 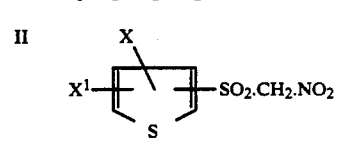 |

| | CHEMICAL FORMULAE |
|---|---|
| III | 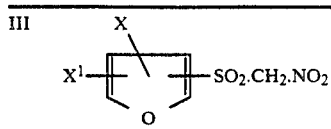 |
| IV | Q.SO$_2^-$M$^+$ |
| V | Q.SO$_2$.CH$_3$ |
| VI | Q.S.CH$_3$ |
| VII | Q.S.CH$_2$.NO$_2$ |
| VIII | Q.SH |
| IX | Q.S.CH$_2$.CO$_2$H |
| XI | Q.S.CH(NO$_2$).CO$_2$H |
| XII | Q.SCl |

[Note: Formula X is not used]

What is claimed is:

1. A nitromethane derivative of the formula I Q.SO$_2$.CH$_2$.NO$_2$ thienyl, benzothienyl, or dibenzothienyl; and wherein Q may optionally bear up to three substituents independently selected from: halogeno, cyano, carboxy, alkylamino or dialkylamino of up to 6 carbon atoms, (1-6C)alkanoylamino, (1-6C)alkanoyl, (1-6C)alkyl, (2-6C)alkenyl, (3-6C)alkenyloxy, (1-6C)alkoxy, fluoro(1-4C)alkoxy, hydroxy(1-6C)alkyl, (1-4C)alkoxy(1-4C)alkyl, carbamoyl, sulphamoyl, (1-6C)alkoxycarbonyl, (1-4C)alkylenedioxy, (1-6C)alkanesulphonamido, alkyl or dialkylcarbamoyl of up to 7 carbon atoms, alkyl or dialkylsulphamoyl of up to 6 carbon atoms, groups of the formula —S(O)$_n$.R$^1$, phenyl, benzyl, phenoxy, benzyloxy, benzamido and enzenesulphonamido, the benzene ring of which last six substituents may itself optionally bear 1 or 2 substituents independently selected from halogeno, (1-4C)alkyl and (1-4C)alkoxy substituents; and when Q is benzothienyl or dibenzothienyl, the optional substituents on Q are also independently selected from hydroxy, amino, nitro and fluoro(1-4C)alkyl; or a non-toxic salt thereof.

2. A compound as claimed in claim 1 wherein Q is thienyl, benzothienyl, or dibenzothienyl; and wherein the group Q is unsubstituted or bears 1, 2 or 3 substituents independently selected from: fluoro, chloro, bromo, iodo, cyano, carboxy, methylamino, ehtylamino, propylamino, butylamino, dimethylamino, diethylamino, (methyl)(propyl)amino, formamido, acetamido, propionamido, formyl, acetyl, propionyl, butyryl, 2,2-dimethylpropionyl, methyl, ethyl, propyl, isopropyl, butyl, sec-butyl, t-butyl, vinyl, allyl, 1-propenyl, 2-methyl-2-propenyl, allyloxy, 2-methyl-2-propenyloxy, 3-methyl-3-butenyloxy, methoxy, ethoxy, propoxy, isopropoxy, butoxy, t-butoxy, trifluoromethoxy, pentafluoroethoxy, hydroxymethyl, 1-hydroxyethyl, 2-hydroxyethyl, 3-hydroxypropyl, methoxymethyl, ethoxymethyl, 1-methoxyethyl, 2-methoxyethyl, 3-methoxypropyl, methoxycarbonyl, ethoxycarbonyl, isopropoxycarbonyl, t-butoxycarbonyl, methylenedioxy, ethylenedioxy, isopropylidenedioxy, any of which latter three groups being attached to adjacent atoms of the aromatic moiety Q, carbamoyl, sulphamoyl, methanesulphonamido, ethanesulphonamido, butanesulphonamido, N-methylcarbamoyl, N,N-dimethylcarbamoyl, N-ethylcarbamoyl, N,N-diethylcarbamoyl, N,N-dipropylcarbamoyl, N-methylsulphamoyl, N-ethylsulphamoyl, N-propylsulphamoyl, N-butylsulphamoyl, N,N-dimethylsulphamoyl, methylthio, ethylthio, propylthio, butylthio, methylsulphinyl, ethylsulphinyl, methylsulphonyl, ethylsulphonyl, phenyl, benzyl, phenoxy, benzyloxy, benzamido and benzenesulphonamido, any of which last six groups may optionally bear 1 or 2 fluoro, chloro, bromo, methyl, ethyl, methoxy or ethoxy substituents; and when Q is benzothienyl or dibenzothienyl, the optional substituents on Q are also independently selected from hydroxy, amino, nitro, trifluoromethyl, pentafluoroethyl and 2,2,2-trifluoropropyl; or a non-toxic salt thereof.

3. A thiophene derivative of the formula II

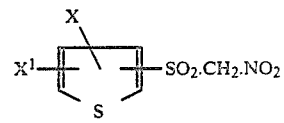

wherein X is selected from hydrogen, halogeno, cyano, (1-6C)alkyl, (1-6C)alkanoyl, (1-6C)alkoxy and benzyl, the latter itself optionally bearing 1 or 2 substituents selected from halogeno, (1-4C)alkyl and (1-4C)alkoxy; and X$^1$ is hydrogen, halogeno or (1-6C)alkyl; or a non-toxic salt thereof.

4. A compound as claimed in claim 3 wherein X is selected from hydrogen, chloro, bromo, iodo, methyl, methoxy, t-butoxy and 2,2-dimethylpropionyl; and X$^1$ is hydrogen, fluoro, chloro, bromo, iodo, methyl or ethyl; or a non-toxic salt thereof.

5. A nitromethane derivative of the formula I Q.SO$_2$.CH$_2$NO$_2$ wherein Q is benzo[b]thienyl, which group is unsubstituted or bears 1 or 2 substituents independently selected from any of the values for X as defined in claim 3; or a non-toxic salt thereof.

6. A compound of formula I Q.SO$_2$.CH$_2$NO$_2$ selected from:

2-(nitromethylsulphonyl)thiophene,
2-chloro-5-(nitromethylsulphonyl)thiophene,
2-methoxy-5-(nitromethylsulphonyl)thiophene,
3-bromo-2-methoxy-5-(nitromethylsulphonyl)thiophene,
2-(nitromethylsulphonyl)benzo[b]thiophene,
4-bromo-2-(nitromethylsulphonyl)thiophene,
2-bromo-5-(nitromethylsulphonyl)thiophene,
2-iodo-5-(nitromethylsulphonyl)thiophene,
4-methyl-2-(nitromethylsulphonyl)thiophene, or a non-toxic salt thereof.

7. A non-toxic salt as claimed in claim 1 which is a pharmaceutically acceptable salt selected from alkali metal, alkaline earth metal, ammonium and aluminium salts, and salts with organic bases affording physiologically acceptable cations, and for those compounds of formula I which contain an alkylamino or dialkylamino substituent on Q, in addition, physiologically acceptable acid addition salts with a hydrogen halide, sulphuric acid, phosphoric acid, citric acid and maleic acid.

8. A pharmaceutical composition which comprises an aldose reductase inhibitory amount of a nitromethane derivative of the formula I or II, or a non-toxic salt thereof, as claimed in claim 1 or 3, respectively, together with a pharmaceutically acceptable diluent or carrier.

9. A method of inhibiting the enzyme aldose reductase in a warm-blooded animal requiring such treatment which comprises administering to said animal an effective amount of a nitromethane derivative of the formula I, or a non-toxic salt thereof, as defined in claim 1.

10. The derivative according to claim 1 wherein Q is thienyl.

* * * * *